(12) United States Patent
Chen et al.

(10) Patent No.: US 7,449,300 B2
(45) Date of Patent: Nov. 11, 2008

(54) DETECTION OF ANTIBODIES SPECIFIC FOR B7-H1 IN SUBJECTS WITH DISEASES OR PATHOLOGICAL CONDITIONS MEDIATED BY ACTIVATED T CELLS

(75) Inventors: Lieping Chen, Rochester, MN (US); Scott E. Strome, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 261 days.

(21) Appl. No.: 10/719,477

(22) Filed: Nov. 21, 2003

(65) Prior Publication Data
US 2004/0180047 A1    Sep. 16, 2004

Related U.S. Application Data

(60) Provisional application No. 60/428,132, filed on Nov. 21, 2002.

(51) Int. Cl.
*G01N 33/53* (2006.01)
(52) U.S. Cl. .................................................. 435/7.1
(58) Field of Classification Search .............. None
See application file for complete search history.

(56) References Cited

U.S. PATENT DOCUMENTS

| 2002/0102651 A1 | 8/2002 | Freeman et al. |
| 2003/0044768 A1 | 3/2003 | Wood et al. |
| 2006/0153841 A1 | 7/2006 | Freeman et al. |

FOREIGN PATENT DOCUMENTS

WO    WO01/14556    3/2001

OTHER PUBLICATIONS

Uhlig et al., 2005, Ann. Rheum. Disease, 64: 7-10.*
Dong et al., J. Clin. Investigat., 2003, 111: 363-370.*
Merrill et al., Best Practice and Research Clinical Rheumatology, 2005, 19: 709-726.*
Dong et al., 1999, Nature Medicine, 5: 1365-1369 (reference provided by Applicant).*
MacKenzie (2006) Drug Discovery Today 11(19): 952-956 (reference provided by Applicant).*
Silverman (2006) Bulletin of the NYU Hospital for Joint Diseases 64(1 and 2) :51-56 (reference provided by Applicant).*
Solares et al. (2003) J. Neuroimmunol. 138: 1-7 (reference provided by Applicant).*
Klippel (1997) J. Rheumatol. 24(suppl. 48):67-71 (reference provided by Applicant).*
Bovo et al. (2006) Acta Oto-Laryngologica 126: 1012-1021 (reference provided by Applicant).*
Experimental data generated by a licensee of the present application.

* cited by examiner

*Primary Examiner*—Ilia Ouspenski
(74) *Attorney, Agent, or Firm*—Millen, White, Zelano, Branigan, P.C.

(57) ABSTRACT

The invention provides methods of removing B7-H1-specific antibodies from a body fluid (e.g., blood), methods of diagnosing and treating diseases and pathological conditions mediated by activated T cells, methods for screening for compounds that inhibit binding of a B7-H1-specific antibody to B7-H1, and methods of designing compounds that inhibit binding of a B7-H1-specific antibody to B7-H1.

11 Claims, 6 Drawing Sheets

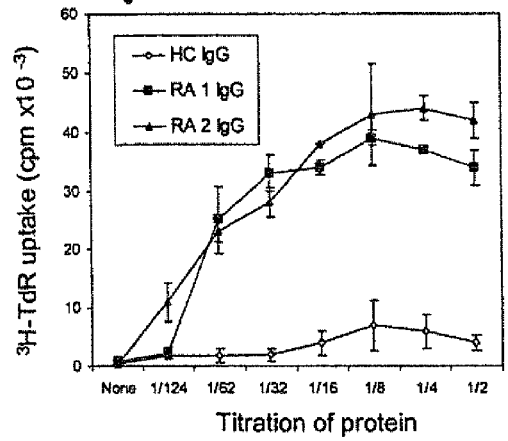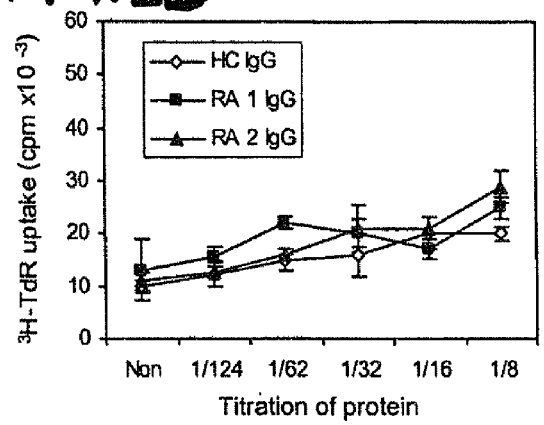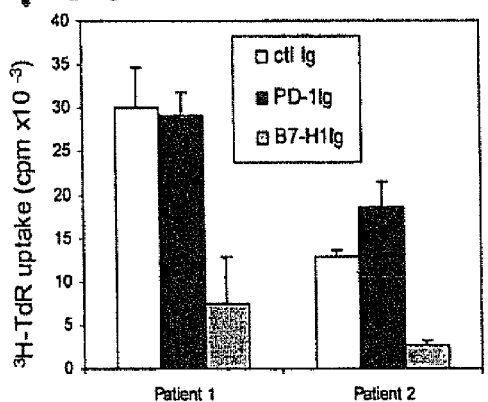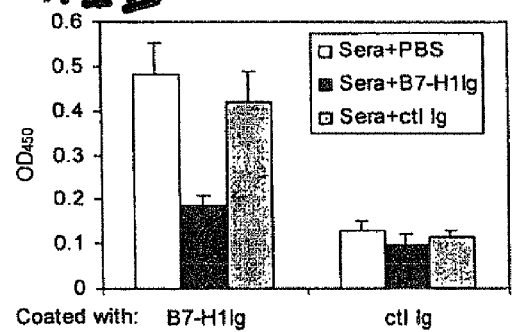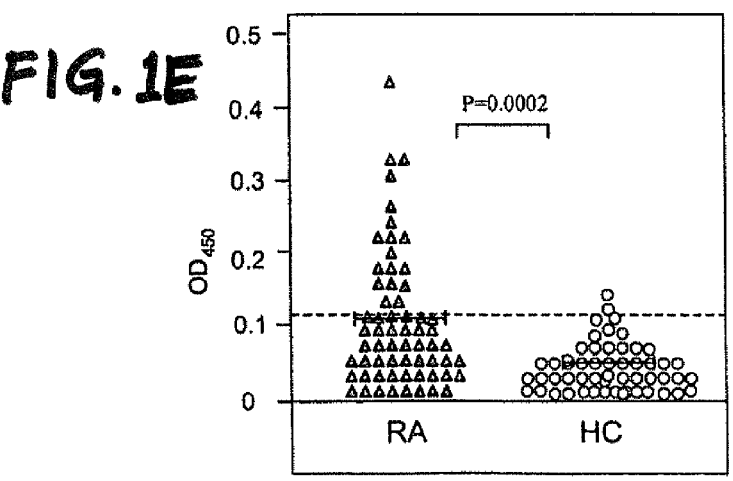

FIG. 2A
Mock/293 cells    B7-H1/293 cells
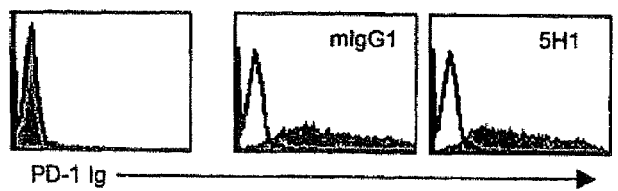
PD-1 Ig →
M99 CTL
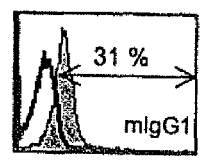
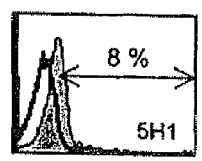
B7-H1 Ig →
FIG. 2B
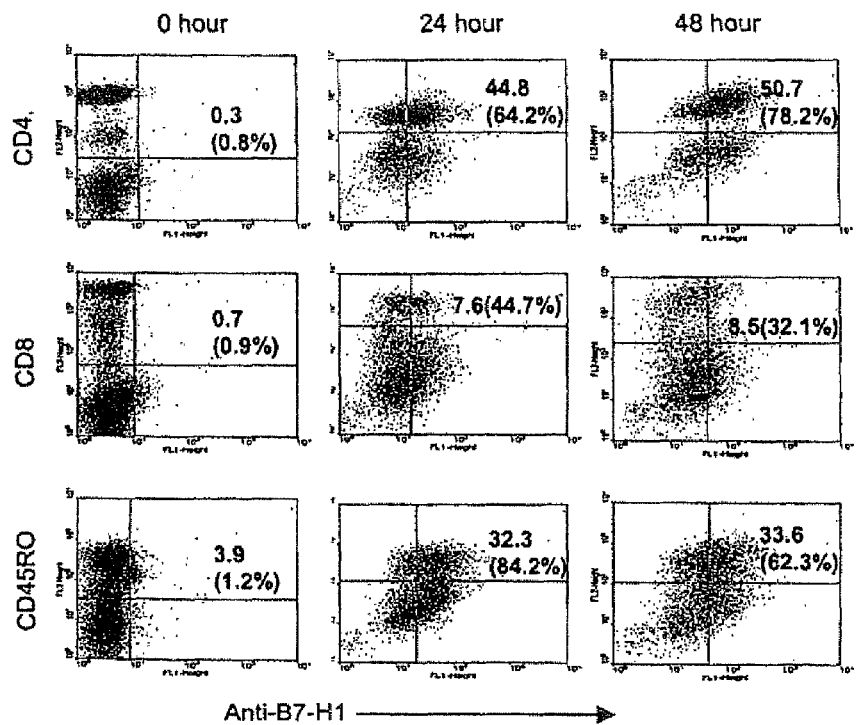
Anti-B7-H1 →

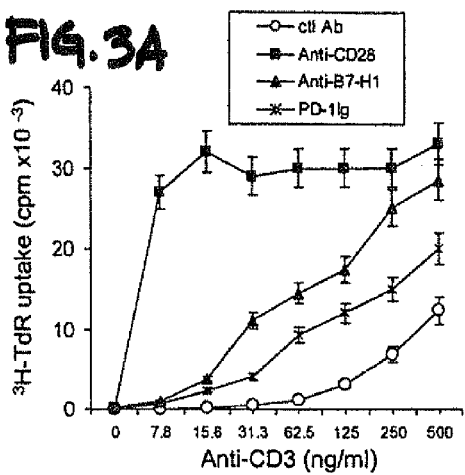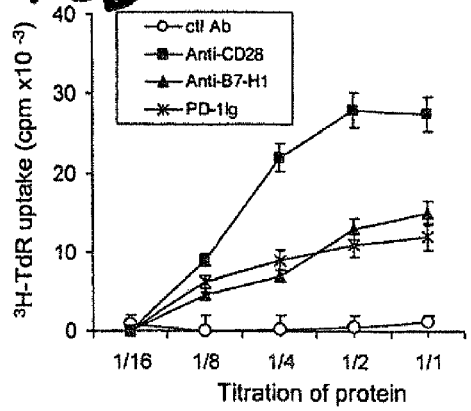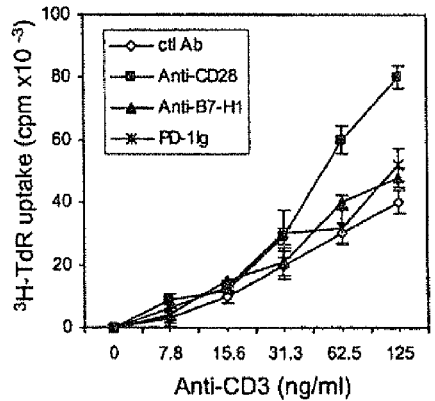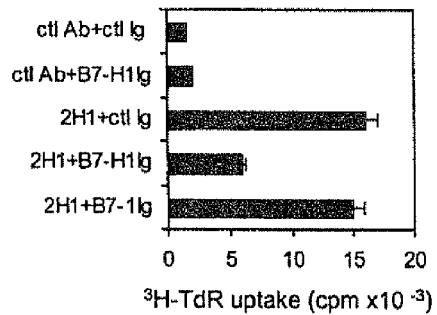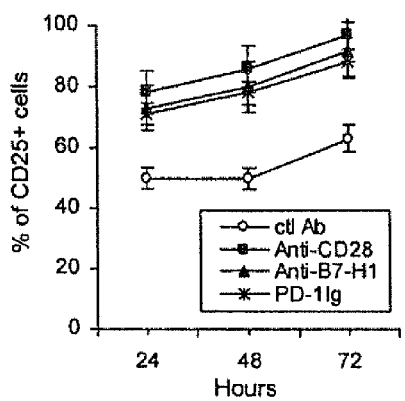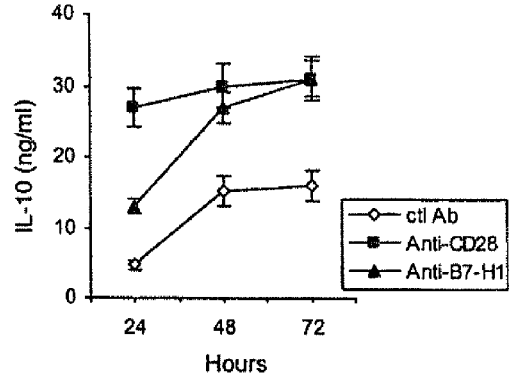

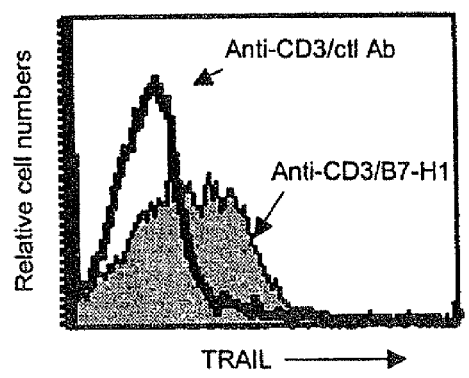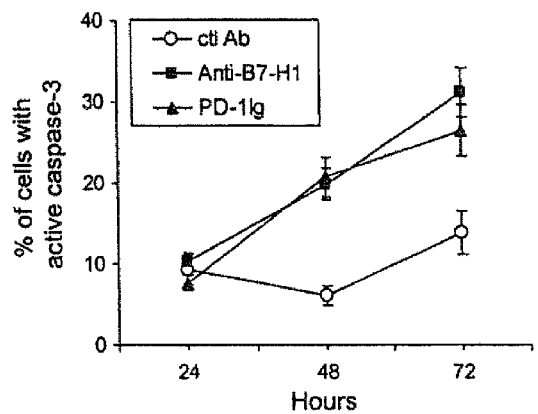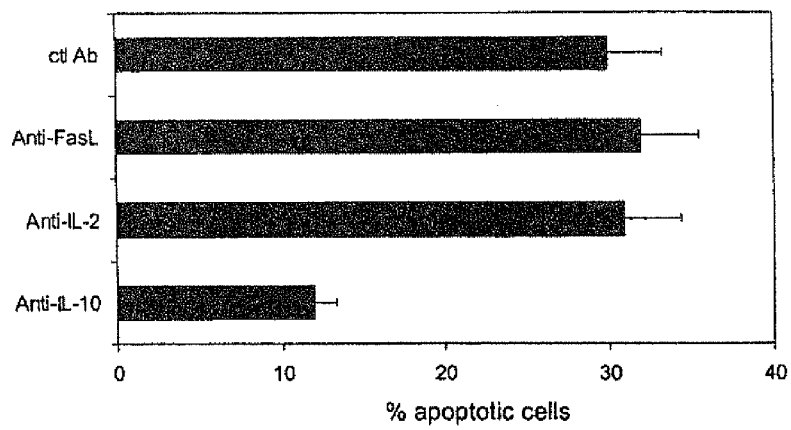

US 7,449,300 B2

DETECTION OF ANTIBODIES SPECIFIC FOR B7-H1 IN SUBJECTS WITH DISEASES OR PATHOLOGICAL CONDITIONS MEDIATED BY ACTIVATED T CELLS

This application claims priority of U.S. Provisional Application No. 60/428,132, filed Nov. 21, 2002. The disclosure of U.S. Provisional Application No. 60/428,132 is incorporated herein by reference in its entirety.

TECHNICAL FIELD

This invention relates to diseases involving the immune system, and more particularly to activated T cell-mediated diseases.

BACKGROUND

Diseases and other pathological conditions mediated by activated T cells remain a significant problem. Causes of the aberrant T cell activity implicated in these diseases and pathological conditions and ways to treat them remain elusive.

SUMMARY

The invention is based in part on the findings that: (a) sera from rheumatoid arthritis (RA) patients contain costimulatory autoantibodies specific for the B7-H1 molecule; (b) the presence of the B7-H1 autoantibodies in sera correlate with active disease in the patients; (c) B7-H1 is expressed on activated but not unactivated T cells; and (d) binding of antibodies to B7-H1 on T cells provides a costimulatory signal to the T cells. Similarly, the inventors have observed autoantibodies specific for B7-H1 in the sera of patients with systemic lupus erythematosus (SLE) and autoimmune hearing loss (AHL). These findings suggest that autoantibodies specific for B7-H1 may cause, or cause exacerbation of, diseases or pathological conditions whose symptoms are caused directly, or indirectly, by activated T cells, e.g., autoimmune diseases such as RA, multiple sclerosis (MS), insulin-dependent diabetes mellitus (IDDM), systemic lupus erythematosus (SLE), AHL, and myasthenia gravis (MG), allergies (including delayed as well as immediate type hypersensitivity reactions) to any of a wide range of allergen such as asthma or chronic sinusitis, and rejection of allografts and xenografts. The invention thus provides methods for removing antibodies specific for B7-H1 from body fluids and other methods of treatment, methods of diagnosis, methods of assessing the stage of a disease, and methods of identifying and designing compounds that inhibit the binding of B7-H1 to antibodies specific for B7-H1.

More specifically, the invention includes a method of removing antibodies specific for B7-H1 from a body fluid of a subject. The method involves: (a) withdrawing a body fluid from a subject, the body fluid containing one or more antibodies that bind to (i.e., are specific for) B7-H1; (b) removing from the body fluid a substantial portion of the one or more antibodies; and (c) returning the body fluid to the subject. The body fluid can be, for example, blood plasma. The subject can be one suspected of having a disease or pathological condition, or is likely to develop a disease or pathological condition, with symptoms that are caused directly, or indirectly, by activated T cells. The disease or pathological condition can be, for example, an autoimmune disease such as rheumatoid arthritis (RA), systemic lupus erythematosus (SLE), or autoimmune hearing loss (AHL). The removal can include contacting the body fluid with a B7-H1 reagent and the B7-H1 reagent can be bound to a solid support. Prior to the removal step, the blood plasma can be separated from blood cells.

Also encompassed by the invention is a method of treatment that includes: (a) identifying a subject as having an elevated level in a body fluid of one or more B7-H1-specific antibodies; and (b) administering to the subject one or more compounds that inhibit the binding of B7-H1 to one or more B7-H1-specific antibodies. The body fluid can be, for example, blood. The subject can be any of those listed above and the compound can contain or be B7-H1 or a fragment of B7-H1.

Another aspect of the invention is a method of diagnosis that involves: (a) identifying a subject that is suspected of having, or is likely to develop, a disease or pathological condition with symptoms that are caused directly, or indirectly, by activated T cells; (b) obtaining a sample of body fluid from the subject; and (c) detecting one or more B7-H1-specific antibodies in the sample, an elevated level of one more B7-H1-specific antibodies in the sample being an indication that the subject has, or is likely to develop, a disease or pathological condition with symptoms that are caused directly, or indirectly, by activated T cells. The disease or pathological condition can be any of those recited above.

The invention also embraces a method of monitoring the progress of a disease or pathological condition. The method includes: (a) identifying a subject that is suspected of having a disease or pathological condition, or is likely to develop a disease pathological condition, with symptoms that are caused directly, or indirectly, by activated T cells.; (b) obtaining a sample of a body fluid from the subject; and (c) measuring the level of one or more B7-H1-specific antibodies in the sample, the level of one or more B7-H1-specific antibodies in the sample correlating with the stage of the disease or pathological condition. Steps (b) and (c) can be repeated one or more times. The disease or pathological condition can be any of those listed above and the body fluid can be blood.

In another the aspect, the invention provides a method of identifying a compound that inhibits binding of B7-H1 to an antibody that binds to B7-H1. The method includes contacting B7-H1 with the antibody in the presence of the compound and testing for inhibition by the compound of binding of B7-H1 to the antibody.

Also featured by the invention is a method of designing a compound that inhibits the binding of B7-H1 to an antibody that binds to B7-H1. The method involves analyzing the three dimensional structure of B7-H1, or a fragment of B7-H1, and designing a compound with a three-dimensional structure that corresponds to an external portion of B7-H1, the compound binding to an antibody that binds to B7-H1.

Another method provided by the invention is one of inhibiting expression of B7-H1 in a T cell. The method can involve introducing into the T cell: (a) an antisense oligonucleotide that hybridizes to a B7-H1 transcript, the antisense oligonucletide inhibiting expression of B7-H1 in the cell; or (2) a B7-H1 interference RNA (RNAi). The introducing step can include administration of the antisense oligonucleotide or the RNAi to the cell and uptake of the antisense oligonucleotide or the RNAi by the cell. Alternatively, the introducing step can include administering to the cell a nucleic acid that contains a transcriptional regulatory element (TRE) operably linked to a nucleotide sequence complementary to the antisense oligonucleotide, transcription of the nucleotide sequence inside the cell producing the antisense oligonucleotide. In addition, the introducing step can involve administering to the T cell a nucleic acid: (a) from which sense and anti-sense strands of the RNAi can be transcribed under the direction of separate TREs; or (b) from which both sense and anti-sense strands of the RNAi can be transcribed under the direction of a single TRE. The cell can be in vitro or in a mammal. The mammal can be a human or any other mammal recited herein.

"Polypeptide" and "protein" are used interchangeably and mean any peptide-linked chain of amino acids, regardless of length or post-translational modification. Polypeptides useful in the invention include variant polypeptides that are identical to corresponding wild-type polypeptides but differ by not more than 50 (e.g., not more than: 45; 40; 35; 30; 25; 23; 20; 19; 18; 17; 16; 15; 14; 13; 12; 11; 10; nine; eight; seven; six; five; four; three; two; or one) conservative substitution(s). All that is required is that the variant polypeptide have at least 20% (e.g., at least: 25%; 30%; 35%; 40%; 45%; 50%; 60%; 70%; 80%; 85%; 90%; 93%; 95%; 96%; 97%; 98%; 99%; 99.5%; 99.8%; 99.9%, or 100% or more) of the activity of the wild-type polypeptide. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

As used herein, a B7-H1-specific antibody that "co-stimulates" a T cell is a B7-H1-specific antibody that, upon interaction with a B7-H1 molecule on the T cell, enhances the response of the T cell. The T cell response that results from the interaction will be greater than the response in the absence of the antibody. The response of the T cell in the absence of the co-stimulatory antibody can be no response or it can be a response significantly lower than in the presence of the co-stimulatory antibody. It is understood that the response of the T cell can be an effector (e.g., CTL or antibody-producing B cell) response, a helper response providing help for one or more effector (e.g., CTL or antibody-producing B cell) responses, or a suppressive response.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., treating T cell-mediated diseases, will be apparent from the following description, from the drawings and from the claims.

DESCRIPTION OF DRAWINGS

FIG. 1A is a line graph showing the proliferative responses (in counts per minute ("cpm×10$^{-3}$")) of $^3$H-thymidine uptake ("$^3$H-TdR uptake")) of human CD4+ T cells in the presence of a suboptimal concentration of immobilized anti-CD3 monoclonal antibody (mAb) and various concentrations of immobilized IgG purified from RA patient 1 ("RA 1 IgG"; ■), from RA patient 2 ("RA 2 IgG"; ▲), or from a healthy human donor ("HC IgG"; ◇).

FIG. 1B is a line graph showing the proliferative responses (in counts per minute ("cpm×10$^{-3}$")) of $^3$H-thymidine uptake ("$^3$H-TdR uptake")) of human CD4+ T cells in the presence of a suboptimal concentration of immobilized anti-CD3 mAb and various concentrations of soluble IgG purified from RA patient 1 ("RA 1 Ig"; ■), from RA patient 2 ("RA 2 IgG"; ▲), or from a healthy human donor ("HC IgG"; ◇).

FIG. 1C is a bar graph showing the proliferative responses (in terms of counts per minute ("cpm×10$^{-3}$") of $^3$H-thymidine uptake ("$^3$H-TdR uptake")) of human CD4+ T cells in the presence of: immobilized anti-CD3 mAb, immobilized IgG purified from RA patient 1 ("Patient 1") or from RA patient 2 ("Patient 2"); and a blocking agent. The blocking agent was either control IgG ("ctl Ig"; unfilled bars), a fusion protein containing the extracellular domain of human PD-1 ("PD-1Ig"; black filled bars), or a fusion protein containing the extracellular domain of human B7-H1 ("B7-H1Ig"; stippled bars).

FIG. 1D is a bar graph showing the results of a representative ELISA assay to test for the presence of human B7-H1-specific autoantibodies in the serum of a RA patient. Patient serum (diluted 1:1000) that had been preincubated with either PBS only ("Sera+PBS"; unfilled bars), the B7-H1Ig fusion protein ("Sera+B7-H1Ig"; black bars), or control mouse IgG2a ("Sera+ctl Ig"; stippled bars) was added to the wells of ELISA plates coated with either the B7-H1Ig fusion protein ("B7-H1Ig") or control mouse IgG2a ("ctl Ig"). Data are expressed as OD$_{450}$.

FIG. 1E is a scatter graph showing the results of an ELISA assay in which the sera from 63 RA patients ("RA"; stippled triangles) and 54 healthy donors ("HC"; unfilled circles) were tested for the presence of human B7-H1-specific autoantibodies by incubating 1:1000 dilutions of the sera in ELISA plate wells coated with the B7-H1Ig fusion protein as described for FIG. 1D. For each serum sample, a value representing non-specific binding (determined by incubation of the serum sample with control mouse IgG2a-coated ELISA plates) was subtracted from the value obtained with ELISA plate wells coated with the B7-H1Ig fusion protein. The dashed line indicates the "cut off" OD$_{450}$ value (0.123) for positivity and the horizontal bar in the middle of the cluster of data points for healthy donors indicates the mean value for healthy donors.

FIG. 2A is a series of FFC histograms. The cells used to obtain the data in the left histogram of the upper three histograms were mock transfected 293 cells ("Mock/293 cells") and the cells used to obtain the data shown in the middle and right histogram of the upper three histograms were 293 cells transfected with and expressing cDNA encoding human B7-H1 ("B7-H1/293 cells"). The cells shown in all three histograms were stained with 5 μg of the PD-1Ig fusion protein ("PD-1Ig"; filled profiles) or control mouse IgG2a (unfilled profiles). Control mouse IgG1 (20 μg) ("mIgG1") was added to the sample of the middle histogram stained with the PD-1Ig fusion protein and the 5H1 human B7-H1-specific mAb (20 μg) ("5H1") was added to sample of the right panel stained with the PD-1Ig fusion protein; these additions were made prior to the addition of the PD-1Ig fusion protein.

Figure 1F:
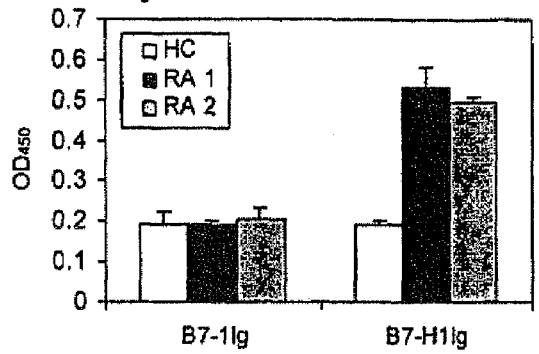
FIG. 1F is a bar graph showing the results of a representative ELISA assay in which the sera from a healthy human donor ("HC"; unfilled bars) and two RA patients ("RA 1"(black bars) and "RA 2" (stippled bars)) were tested for the presence of human B7-H1-specific autoantibodies ("B7-H1Ig") as described for FIGS. 1D and 1E and human B7-1-specific autoantibodies ("B7-1Ig"). The ELISA for the human B7-1 specific autoantibodies was identical to that for human B7-H1-specific autoantibodies except that the relevant ELISA plate wells were coated with a fusion protein containing the extracellular domain of human B7-1 (B7-1Ig) rather than with the B7-H1Ig fusion protein.

The cells used to obtain the data in bottom two histograms were activated M99 cytotoxic T lymphocytes (CTL). The cells were stained with 10 μg of either the B7-H1Ig fusion protein (filled profiles) or control mouse IgG2a (unfilled profiles). Cells stained with the B7-H1Ig fusion protein were incubated with 10 μg of either mouse IgG1 ("mIgG1") or the 5H1 human B7-H1-specific mAb ("5H1") prior to addition of the B7-H1Ig fusion protein. The percentages of cells in the interval indicated by the double-headed arrows are given.

FIG. 2B is series of two-dimensional FFC histograms showing the expression of B7-H1 on human CD4-expressing ("CD4"), CD8-expressing, and CD45RO-expressing peripheral blood mononuclear cells after 0 hours ("0 hour"), 24 hours ("24 hour"), and 48 hours ("48 hour") of stimulation with phytohemagglutin (PHA). The numbers without parentheses are the percentage of total viable PBMC expressing both B7-H1 and either CD4 (top row of histograms), CD8 (middle row of histograms), or CD45RO (bottom row of histograms). The numbers in parentheses indicate the percentage of B7-H1-expressing cells in CD4+ cells (top row of histograms), CD8+ cells (middle row of histograms), or CD45RO+ cells (bottom row of histograms).

FIG. 3A is a line graph showing the proliferative responses (in counts per minute ("cpm×10$^{-3}$") of $^3$H-thymidine uptake ("$^3$H-TdR uptake")) of human CD4+ T cells in the presence of a various amounts of immobilized anti-CD3 mAb ("Anti-CD3") and immobilized (at 10 μg/ml) control antibody ("ctl Ab"; ○), human B7-H1-specific mAb ("Anti-B7-H1"; ▲), or PD-1Ig fusion protein ("PD-1Ig"; x) or immobilized (at 2 μg/ml) human CD28-specific mAb ("Anti-CD28").

FIG. 3B is a line graph showing the proliferative responses (in counts per minute ("cpm×10$^{-3}$") of $^3$H-thymidine uptake ("$^3$H-TdR uptake")) of human CD4+ T cells in the presence of a suboptimal amount of immobilized (at 30 ng/ml) anti-CD3 mAb and the indicated dilutions of immobilized control antibody ("ctl Ab"; ○), human B7-H1-specific mAb ("Anti-B7-H1"; ▲), the PD-1Ig fusion protein ("PD-1Ig"; x) or human CD28-specific mAb ("Anti-CD28"). The highest concentration ("1/1") of control antibody, human B7-H1-specific mAb, and the PD-1Ig fusion protein used for immobilization was 20 μg/ml and that of human CD28-specific mAb was 4 μg/ml.

FIG. 3C is a line graph showing the proliferative responses (in counts per minute ("cpm×10$^{-3}$") of $^3$H-thymidine uptake ("$^3$H-TdR uptake")) of human CD4+ T cells in the presence of a various amounts of immobilized anti-CD3 mAb ("Anti-CD3") and 20 μg/ml of soluble control antibody ("ctl Ab"; ◇), human B7-H1-specific mAb ("Anti-B7-H1"; ▲), or the PD-1Ig fusion protein ("PD-1Ig"; x) or 2 μg/ml of soluble human CD28-specific mAb ("Anti-CD28").

FIG. 3D is a bar graph showing the proliferative responses (in terms of counts per minute ("cpm×10$^{-3}$") of $^3$H-thymidine uptake ("$^3$H-TdR uptake")) of human CD4+ T cells in the presence of: a suboptimal concentration of immobilized anti-CD3 mAb and either immobilized control antibody ("ctl Ab") or immobilized 2H1 human B7-H1-specific mAb ("2H1"). Before addition of the CD4+ T cells to the culture wells, control IgG2a ("ctl Ig"), the B7-H1Ig fusion protein ("B7-H1Ig"), or the B7-1Ig fusion protein ("B7-1Ig") was added to the wells and incubated with the relevant immobilized antibodies.

FIG. 3E is line graph showing the number of interleukin-2 receptor (CD25) expressing cells in CD4+ cells ("% of CD25+ cells") after stimulation for 24, 48, and 72 hours with immobilized anti-CD3 mAb and immobilized control antibody ("ctl Ab"; ○), human CD28-specific mAb ("Anti-CD28"; ■), human B7-H1-specific mAb ("Anti-B7-H1"; ▲), or the PD-1Ig fusion protein ("PD-1Ig"; x).

FIG. 3F is a line graph showing the amounts of interleukin-10 ("IL-10") secreted by CD4+ T cells stimulated with immobilized anti-CD3 mAb and immobilized control antibody ("ctl Ab"; ○), human CD28-specific mAb ("Anti-CD28"; ■), human B7-H1-specific mAb ("Anti-B7-H1"; ▲).

Figure 4A:
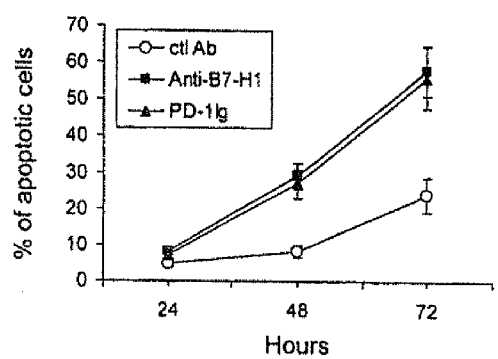

FIG. 4A is a line graph showing the percentage of apoptotic cells (those staining with Annexin V but not with propidium iodide) in human CD4+ T cells after culture with an optimal amount of immobilized anti-CD3 mAb and immobilized control mAb ("ctl Ab"; ○), human B7-H1-specific mAb ("Anti-B7-H1"; ■), or PD-1Ig fusion protein ("PD-1Ig"; ▲).

Figure 4B:
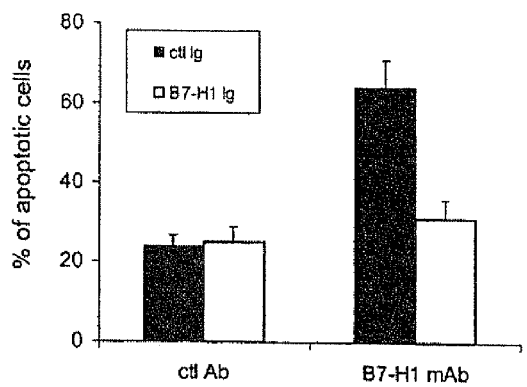

FIG. 4B is a bar graph showing the percentage of apoptotic cells (detected as described for FIG. 4A) in human CD4+ T cells after culture with an optimal amount of immobilized anti-CD3 mAb and immobilized control mAb ("ctl Ab") or human B7-H1-specific mAb ("B7-H1 mAb"). Before addition of the CD4+ T cells to the culture wells, control IgG2a ("ctl Ig") or the B7-H1Ig fusion protein ("B7-H1Ig") was added to the wells and incubated with the immobilized antibodies.

Figure 4C:
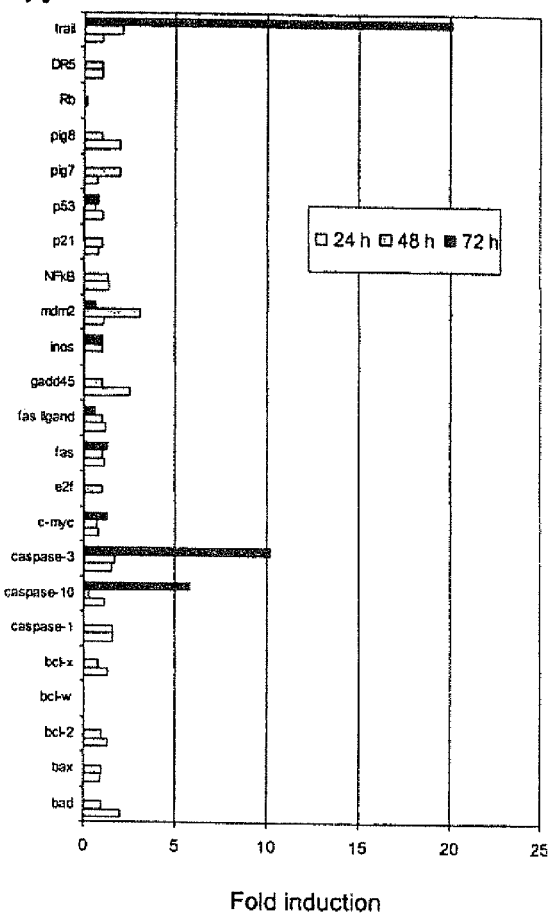

FIG. 4C is a bar graph showing the expression of apoptosis-related genes by CD4+ human T cells after culture for 24 hours (unfilled bars), 48 hours (stippled bars) and 72 hours (black bars) with an optimal amount of immobilized anti-CD3 mAb and immobilized control antibody ("ctl Ab") or human B7-H1-specific mAb ("B7-H1 mAb"). Data are expressed as "Fold induction", i.e., the ratio of the level of mRNA transcribed from a particular gene in CD4+ T cells costimulated with the human B7-H1-specific mAb to the level of mRNA transcribed from the same gene in CD4+ T cells exposed to the control mAb.

FIG. 4D is a FFC histogram showing the expression of TRAIL protein by human CD4+ T cells after stimulation with immobilized anti-CD3 antibody and either a control antibody ("Anti-CD3/ctl Ab") (unfilled profile) or human B7-H1-specific mAb ("Anti-CD3/B7-H1") (filled profile).

FIG. 4E is a line graph showing the percentage of CD4+ T cells expressing active caspase-3 ("% of cells with active caspase-3"), as detected by FFC analysis of FAM-DEVD-FMK-stained cells, after culture with immobilized anti-CD3 mAb and either immobilized control antibody ("ctl Ab"; ○), human B7-H1-specific mAb ("Anti-B7-H1"; ■), or the PD-1Ig fusion protein ("PD-1Ig"; ▲).

FIG. 4F is a bar graph showing the percentage of apoptotic cells (detected as described for FIG. 4A) in human CD4+ T cells after culture with an optimal amount of immobilized anti-CD3 mAb, immobilized human B7-H1-specific mAb, and either soluble control antibody ("ctl Ab"), soluble Fas ligand-specific mAb ("Anti-FasL"), soluble interleukin-2-specific mAb ("Anti-IL-2"), or soluble interleukin-10-specific mAb ("Anti-IL-10").

DETAILED DESCRIPTION

B7-H1 is a molecule that has been shown previously to be expressed on antigen presenting cells (APC) and to costimulate T cells by interacting with one or more receptors on the T cells. The experiments outlined at the beginning of the Summary section indicate that B7-H1 molecules are also expressed on activated T cells and that, in subjects with diseases or pathological conditions mediated directly or indirectly by activated T cells, autoantibodies specific for B7-H1 molecules are produced and that at least some of the autoantibodies that the subjects produce costimulate the responses of T cells (e.g., autoantigen-specific T cells) by binding to the B7-H1 molecules on the surface of the T cells. An alternative mechanism by which B7-H1-specific autoantibodies to B7-H could be acting is one in which the B7-H1-specific antibodies sterically block B7-H1 from interacting with PD-1 on T cells, this leading to decreased negative signaling via PD-1 to the T cells. Several lines of evidence, however, do not support this hypothesis. Thus, only immobilized B7-H1 antibodies induced reverse costimulation of B7-H1-expressing T cells; soluble antibodies did not (Examples 2 and 4). This result emphasizes the importance of cross-linking rather than neutralizing B7-H1-specific antibodies in the activation of T cells. Furthermore, the 5H1 B7-H1-specific monoclonal antibody (mAb) did not block the interaction between B7-H1 and PD-1, while it partially inhibited binding of B7-H1 to a non-PD-1 receptor on M99 T cells (Example 4), indicating that steric blocking of B7-H1 by antibodies under the described experimental conditions would still allow B7-H1 to interact with PD-1. Consistent with these findings, reverse costimulation by B7-H1 autoantibodies could not be blocked by PD-1Ig fusion protein (Example 1). Taken together, our results suggest that inhibition of PD-1-mediated negative signaling to T cells is not the mechanism by which B7-H1-specific antibodies activate T cells. However, the invention is not limited by any particular mechanism of action.

The presence of autoantibodies to B7-H1 in the sera of RA patients raised the question of why immunological tolerance to B7-H1 is broken in these patients. In this regard, B7-H1 expression was not detected on freshly isolated T cells from ten RA patients (unpublished observation). This observation may have been a consequence of the transient nature of B7-H1 expression on T cells and/or the anti-inflammation therapy the patients were undergoing. The inventors have previously observed that the B7-H1 mRNA can be detected in various organs including heart, lung, liver, placenta and spleen in healthy individuals. However, immunohistochemical analysis using B7-H1 mAb showed no evidence of B7-H1 protein expression, except in macrophage-lineage cells, including Kupffer cells of the liver and monocytes in blood. Expression of B7-H1 protein, however, can be induced in cells such as activated T cells [Dong et al. (1999) Nature Med. 5:1365-1369; Tamura et al. (2001) Blood 97:1809-1816]. It is thus possible that, in autoimmune diseases and any other diseases or pathological conditions mediated by activated T cells, inflammatory reactions of any of a variety of cell types may lead to ectopic expression of B7-H1 and the abnormally expressed B7-H1 might in turn serve as an antigen source for elicitation of autoantibodies. The invention is not limited by the mechanism by which the production of autoantibodies specific for B7-H1 is elicited in relevant subjects.

Various aspects of the invention are described below.

Removal of Antibodies Specific for B7-H1 from a Body Fluid

The invention provides a method of removing antibodies specific for B7-H1 from a body fluid of a subject. The method involves: (a) withdrawing a body fluid from a subject, the body fluid containing one or more antibodies that bind to B7-H1; (b) removing from the body fluid a substantial portion of the one or more antibodies; and (c) returning the body fluid to the subject. As used herein, a "substantial portion of the one or more antibodies" means at least 20% (e.g., at least: 20%; 30%; 40%; 50%; 60%; 65%; 70%; 75%; 80%; 85%; 90%; 93%; 95%; 96%; 97%; 98%; 99%; 99.5%; 99.8%; or even 100%) of the antibodies in the body fluid prior to removal. The body fluid can be blood plasma or any other body fluid, e.g., lymph or cerebrospinal fluid.

The subject can be one that is suspected of having a disease or pathological condition, or is likely to develop a disease or pathological condition, with symptoms that are caused directly, or indirectly, by activated T cells (e.g., CD4+ or CD8+ T cells). Prior to withdrawal of the body fluid, the subject can have been identified (by methods known in the art) to be in one of these categories.

The disease can be an autoimmune disease, e.g., RA, SLE, autoimmune hearing loss (AHL), multiple sclerosis (MS), myasthenia gravis (MG), or insulin-dependent diabetes mellitus (IDDM). Other pathological conditions that can be treated by the method include allergies (e.g., delayed type as well as immediate type hypersensitivity reactions) to any of a wide range of allergens (e.g., fungal spores, animal dander, or plant pollens such as ragweed pollen) such as asthma or chronic sinusitis. Delayed type hypersensitivity (DTH) responses are T cell mediated reactions to an allergen. While the pathology in immediate type hypersensitivity (ITH) is due to antibodies (e.g., IgE antibodies), the methods of the invention are applicable to the treatment of ITH in that antibody responses of B cells are generally dependent on the activity of activated "helper" T cells. Moreover, in that the rejection of allografts and xenografts (e.g., kidney, liver, heart, lung, intestinal tissue, bone marrow, pancreatic islet, hepatocyte, or stem cell allografts and xenografts) is due in large part to the activity of T cells (e.g., cytotoxic, inflammatory, and helper T cells), the methods of the invention are applicable to the prevention or treatment of it. In light of the inventors' findings described herein, it is likely that depleting B7-H1-specific antibodies from subjects with one of the above diseases or pathological conditions will result in an decrease in the symptoms of the disease or pathological condition.

Antibodies removed can be of any class, e.g., IgG (such as IgG1, IgG2 (for example IgG2a or IgG2b), IgM, IgD, IgA, or IgE antibodies. Subjects, B7-H1 molecules, and antibodies can be of any mammalian species, for example, human, non-human primate (e.g., monkey or chimpanzee), horse, cow, sheep, goat, pig, cat, dog, rabbit, guinea pig, rat, hamster, gerbil, or mouse.

The antibody removal can be by contacting the body fluid with full-length mature or immature B7-H1, a fragment of mature or immature B7-H1 (e.g., the extracellular domain of B7-H1), or a fusion protein containing mature or immature B7-H1 (or a fragment of mature or immature B7-H1), e.g., the fusion protein B7-H1Ig disclosed in Example 1; for convenience these molecules are collectively referred to herein as "B7-H1 reagents".

The B7-H1 reagent can be bound to a solid support. Such solid supports can be manufactured in the form of, without limitation, membranes, fibers, spherical beads, or granules and can be made with a water-insoluble, preferably porous, biocompatible material, e.g.: organic polymers such as agarose, dextran, and polyacrylamide; inorganic porous materials such as porous glass or porous silica gel; synthetic high molecular weight compounds such as polymethyl methacrylate, polyvinyl alcohol, and styrene-divinylbenzene copolymer; porous polymer hard gels made of a natural high molecular weight compound such as cellulose; and mixtures of two or more of these. Such materials should also be suitable for, or adapted for (e.g., derivatized with appropriate chemical groups), attachment of a B7-H1 reagent.

Where the body fluid is blood plasma, the blood plasma can be separated from blood cells (e.g., erythrocytes) prior to the antibody removal step. The blood cells can be returned to the subject or not. Where they are returned to the subject they can be returned separately from blood plasma from which the B7-H1-specific antibodies have been removed (e.g., immediately after separation from the blood plasma) or they can be mixed with the B7-H1-specific antibody depleted plasma and then reinfused as a mixture into the subject. Alternatively, they can be returned to the subject after returning of the antibody-depleted plasma. Moreover, in systems where the body fluid (e.g., blood plasma) is not rapidly returned to the subject, a "replacement fluid" (e.g., physiological saline) can be administered to the subject after removal of the fluid.

The system can be a continuous one in which, for example, blood is pumped out of a blood vessel (e.g., an artery or a vein) passed over the solid support and pumped directly back into a blood vessel of the subject. As in non-continuous systems, blood cells can be separated from plasma prior to passing of the plasma over the solid support.

Variations of these methods are known to practitioners in the field.

Methods and extracorporeal systems for apheresis (i.e., the process of withdrawing blood from a subject, removing components from the blood, and returning the blood, or blood depleted of one more components, to the subject) are known in the art (see, for example, U.S. Pat. Nos. 4,708,713; 5,258,503; 5,386,734; and 6,409,696, whose disclosures are incorporated herein by reference in their entirety).

Methods of Diagnosis

Another aspect of the invention is a method of diagnosis. The method involves obtaining a sample of body fluid from subject and detecting antibodies that bind to B7-H1 in the sample. The subject can be one that is suspected of having, or is likely to develop, a disease or pathological condition with symptoms that are caused directly, or indirectly, by activated T cells (see above). An elevated level of antibodies that bind to B7-H1 in the sample is an indication that the subject has, or is likely to develop, a disease or pathological condition with symptoms that are caused directly, or indirectly, by activated T cells. The disease or pathological condition and the body fluid can be any of those recited herein.

In the assays of the invention the level of B7-H1-specific antibody is measured in a liquid sample such as a body fluid (e.g., urine, saliva, semen, blood, or serum or plasma derived from blood) or a lavage such as a lung lavage, a gastric lavage, a rectal or colonic lavage, or a vaginal lavage.

Methods of detecting B7-H1-specific antibody in a liquid sample (see above) basically involve contacting a sample suspected of containing B7-H1-specific antibody with a B7-H1 reagent and testing for binding of the B7-H1 reagent to a component of the sample. In such assays the B7-H1 reagent need not be detectably labeled and can be used without a detecting antibody that binds to the B7-H1 reagent. For example, by exploiting the phenomenon of surface plasmon resonance, a B7-H1 reagent bound to an appropriate solid substrate is exposed to the sample. Binding of antibody in the sample to the B7-H1 reagent on the solid substrate results in a change in the intensity of surface plasmon resonance that can be detected qualitatively or quantitatively by an appropriate instrument, e.g., a BIACORE® apparatus (Biacore International AB, Rapsgatan, Sweden).

Moreover, assays for detection of B7-H1-specific antibody in a liquid sample can involve the use, for example, of: (a) a B7-H1 reagent that is detectably labeled; (b) an unlabeled B7-H1 reagent and a detectably labeled detecting antibody that binds to the B7-H1 reagent; or (c) a biotinylated B7-H1 reagent and detectably labeled avidin. In addition, combinations of these approaches (including "multi-layer" assays) familiar to those in the art can be used to enhance the sensitivity of assays. For example, in such assays, the sample or an (aliquot of the sample) suspected of containing B7-H1-specific antibody can be immobilized on a solid substrate such as a nylon or nitrocellulose membrane by, e.g.,"spotting" an aliquot of the liquid sample or by blotting of an electrophoretic gel on which the sample or an aliquot of the sample has been subjected to electrophoretic separation (e.g., Western blotting). The presence or amount of B7-H1-specific antibody on the solid substrate is then assayed using any of the above-described forms of B7-H1 reagent and, where required, appropriate detectably labeled detecting antibodies or avidin.

The invention also features "sandwich" assays. In these sandwich assays, instead of immobilizing samples on solid substrates by the methods described above, any B7-H1-specific antibody that may be present in a sample can be immobilized on the solid substrate by, prior to exposing the solid substrate to the sample, conjugating a capture immunoglobulin-specific antibody (preferably polyclonal) to the solid substrate by any of a variety of methods known in the art. In exposing the sample to the solid substrate with the B7-H1-specific antibody bound to it, any antibody, including B7-H1-specific antibody, in the sample will bind to the capture immunoglobulin-specific antibody on the solid substrate. The presence or amount of B7-H1-specific antibody bound to the capture immunoglobulin-specific antibody is then assayed using any of the above described forms of B7-H1 reagent and, as appropriate, relevant detectably labeled detecting antibodies or avidin. It is understood that in these sandwich assays, the capture immunoglobulin-specific antibody should not bind significantly to antigen-binding regions of B7-H1 antibodies in the sample since this would inhibit detection of their presence using a B7-H1 reagent.

Alternatively, a B7-H1 reagent can be attached directly, or via a capture antibody, to a solid substrate (as described above for attaching putative B7-H1-specific antibody in a test sample to a solid substrate). The solid support with B7-H1 reagent bound to it is then exposed to the test sample. The presence of B7-H1-specific antibody from the sample (or sample aliquot) bound to the B7-H1 reagent on the solid substrate is detected with: (a) a detectably labeled antibody specific for immunoglobulin; (b) an unlabeled first antibody specific for immunoglobulin and a detectably labeled second antibody specific for immunoglobulin; or (c) a biotin-conjugated antibody specific for immunoglobulin and detectably labeled avidin. Methods involving combinations of these detection techniques that can enhance the sensitivity of the assays are known in the art.

A practitioner in the field will appreciate that in assays using a capture antibody (see above), any subsequent antibody specific for immunoglobulin used for detection should optimally be of a specificity and/or species such that it has little to no binding affinity for the capture antibody.

Suitable solid substrates for use in these assays of the invention include, without limitation, the plastic bottoms and sides of wells of microtiter plates, membranes such as nylon or nitrocellulose membranes, polymeric (e.g., without limitation, agarose, cellulose, or polyacrylamide) beads or particles. It is noted that B7-H1 reagents bound to such beads or particles can also be used for immunoaffinity purification of B7-H1-specific antibodies.

Methods of detecting or for quantifying a detectable label depend on the nature of the label and are known in the art. Appropriate labels include, without limitation, radionuclides (e.g., $^{125}$I, $^{131}$I, $^{35}$S, $^{3}$H, $^{32}$P, or $^{14}$C), fluorescent moieties (e.g., fluorescein, rhodamine, or phycoerythrin), luminescent moieties (e.g., QDOT™ nanoparticles supplied by the Quantum Dot Corporation, Palo Alto, Calif.), compounds that absorb light of a defined wavelength, or enzymes (e.g., alkaline phosphatase or horseradish peroxidase). The products of reactions catalyzed by appropriate enzymes can be, without limitation, fluorescent, luminescent, or radioactive or they may absorb visible or ultraviolet light. Assays using such enzymes for detection are referred to as Enzyme-linked Immunosorbent Assays (ELISA). Examples of detectors include, without limitation, x-ray film, radioactivity counters, scintillation counters, spectrophotometers, colorimeters, fluorometers, luminometers, and densitometers.

It will be appreciated that the above assays can be used for monitoring the progress in a subject of a disease or pathological condition with symptoms that are caused directly, or indirectly, by activated T cells. In these methods, at least one (e.g., at least: 2; 3; 4; 5; 6; 7; 8; 9; 10; 11; 12; 13; 14; 15; 16; 17; 18; 19; 20; 25; 30; 35; 40; 50; 75; 100; or more) sample(s) are obtained from the subject. The level of B7-H1-specific antibodies in the sample correlates with the stage of the disease.

The above methods can also be adapted for identifying a compound that inhibits binding of B7-H1 to an antibody that binds to B7-H1. Such screening methods involve contacting a B7-H1 reagent with the antibody in the presence of the compound and testing for inhibition by the compound of binding of B7-H1 to the antibody. Binding inhibition assays are modifications of those described above and well within the skill of ordinary practitioners in the field. Useful methods of measuring binding that can be adapted for measuring inhibition of binding include, without limitation, plasmon resonance, immunoblotting (Western blotting), and enzyme-linked immunoassays (ELISA). Compounds identified by this method of the invention can be useful for inhibiting the activation of T cells by B7-H1-specific antibodies (see below). The method can be used, for example, to test compounds designed by the method described below.

Methods of Designing Compounds that Inhibit the Binding of B7-H1 to a B7-H1-specific Antibody The first step in designing compounds that inhibit the binding of B7-H1 to a B7-H1-specific antibody is to establish the 3-dimensional (3D) structure of an external region of the B7-H1 molecule. As used herein, an "external region" of a biological molecule (e.g., a protein such as B7-H1) is a region of the molecule, as it occurs naturally, that is exposed to the environment of the molecule. This can be achieved by analyzing the entire mature B7-H1 protein or by analyzing a fragment of the B7-H1 protein, e.g., the extracellular domain of the B7-H1 molecule.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., International Patent Application No. PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER™ (Modeling Of New Structures from Secondary and Tertiary Restraints) (see, e.g., International Application No. PCT/US99/11913, the disclosure of which is incorporated herein by reference in its entirety). Other molecular modeling techniques may also be employed in accordance with this invention [e.g., Cohen et al. (1990) J. Med. Chem. 33: 883-894; Navia et al (1992) Current Opinions in Structural Biology, 2, pp. 202-210; the disclosures of these two articles are incorporated herein by reference in their entirety]. All these methods produce data that are amenable to computer analysis should a computer analysis be desired. Other spectroscopic methods that can also be useful in the method of the invention, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

X-ray Crystallography

X-ray crystallography is based on the diffraction of x-radiation of a characteristic wavelength by electron clouds surrounding the atomic nuclei in a crystal of the molecule of interest. The technique uses crystals of purified biological macromolecules (but these frequently include solvent components, co-factors, substrates, or other ligands) to determine near atomic resolution of the atoms making up the particular biological macromolecule. A prerequisite for solving the 3-D structure of the macromolecule by x-ray crystallography is a well-ordered crystal that will diffract x-rays strongly. The method directs a beam of x-rays onto a regular, repeating array of many identical molecules so that the x-rays are diffracted from the array in a pattern from which the structure of an individual molecule can be retrieved. Well-ordered crystals of, for example, globular protein molecules are large, spherical or ellipsoidal objects with irregular surfaces. The crystals contain large channels between the individual molecules. These channels, which normally occupy more than one half the volume of the crystal, are filled with disordered solvent molecules, and the protein molecules are in contact with each other at only a few small regions. This is one reason why structures of proteins in crystals are generally the same as those of proteins in solution.

Methods of obtaining the B7-H1 molecules and fragments are described below. The formation of crystals is dependent on a number of different parameters, including pH, temperature, the concentration of the biological macromolecule, the nature of the solvent and precipitant, as well as the presence of added ions or ligands of the protein. Many routine crystallization experiments may be needed to screen all these parameters for the combinations that give a crystal suitable for x-ray diffraction analysis. Crystallization robots can automate and speed up work of reproducibly setting up a large number of crystallization experiments (see, e.g., U.S. Pat. No. 5,790,421, the disclosure of which is incorporated herein by reference in its entirety).

Polypeptide crystallization occurs in solutions in which the polypeptide concentration exceeds its solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Crystallizations are generally carried out between 4° C. and 20° C. Substances known as "precipitants" are often used to decrease the solubility of the polypeptide in a concentrated solution by forming an energetically unfavorable precipitating depleted layer around the polypeptide molecules [Weber (1991) Advances in Protein Chemistry, 41:1-36, the disclosure of which is incorporated herein by reference in its entirety]. In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2-4 pentanediol, and many of the polyglycols, such as polyethylene glycol (PEG). The precipitating solutions can include, for example, 13-24% PEG 4000, 5-41% ammonium sulfate, and 1.0-1.5 M sodium chloride, and a pH ranging from 5-7.5. Other additives can include 0.1 M HEPES, 2-4% butanol, 0.1 M or 20 mM sodium acetate, 50-70 mM citric acid, 120-130 mM sodium phosphate, 1 mM ethylene diamine tetraacetic acid (EDTA), and 1 mM dithiothreitol (DTT). These agents are prepared in buffers and are added dropwise in various combinations to the crystallization buffer.

Commonly used polypeptide crystallization methods include the following techniques: batch, hanging drop, seed initiation, and dialysis. In each of these methods, it is important to promote continued crystallization after nucleation by maintaining a supersaturated solution. In the batch method, the polypeptide of interest is mixed with precipitants to achieve supersaturation, and the vessel is sealed and set aside until crystals appear. In the dialysis method, the polypeptide is retained in a sealed dialysis membrane that is placed into a solution containing precipitant. Equilibration across the membrane increases the polypeptide and precipitant concentrations, thereby causing the polypeptide to reach supersaturation levels.

In the preferred hanging drop technique [McPherson (1976) J. Biol. Chem., 251:6300-6306, the disclosure of which is incorporated herein by reference in its entirety], an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide may form.

Another method of crystallization introduces a nucleation site into a concentrated polypeptide solution. Generally, a concentrated polypeptide solution is prepared and a seed crystal of the polypeptide is introduced into this solution. If the concentrations of the polypeptide and any precipitants are correct, the seed crystal will provide a nucleation site around which a larger crystal forms.

Yet another method of crystallization is an electrocrystallization method in which use is made of the dipole moments of protein macromolecules that self-align in the Helmholtz layer adjacent to an electrode (see U.S. Pat. No. 5,597,457, the disclosure of which is incorporated herein by reference in its entirety).

Some proteins may be recalcitrant to crystallization. However, several techniques are available to the skilled artisan to induce crystallization. For example, the removal of flexible polypeptide segments at the amino or carboxyl terminal end of the protein may facilitate production of crystalline protein samples. Removal of such segments can be done using molecular biology techniques or treatment of the protein with proteases such as trypsin, chymotrypsin, or subtilisin.

In diffraction experiments, a narrow and parallel beam of x-rays is taken from the x-ray source and directed onto the crystal to produce diffracted beams. The incident primary beams cause damage to both the macromolecule and solvent molecules. The crystal is, therefore, cooled (e.g., to −220° C. to −50° C.) to prolong its lifetime. The primary beam must strike the crystal from many directions to produce all possible diffraction spots, so the crystal is rotated in the beam during the experiment. The diffracted spots are recorded on a film or by an electronic detector. Exposed film has to be digitized and quantified in a scanning device, whereas the electronic detectors feed the signals they detect directly into a computer. Electronic area detectors significantly reduce the time required to collect and measure diffraction data. Each diffraction beam, which is recorded as a spot on film, is defined by three properties: the amplitude, which is measured from the intensity of the spot; the wavelength, which is set by the x-ray source; and the phase, which is lost in x-ray experiments. All three properties are needed for all of the diffracted beams in order to determine the positions of the atoms giving rise to the diffracted beams. One way of determining the phases is called Multiple Isomorphous Replacement (MIR), which requires the introduction of exogenous x-ray scatterers (e.g., heavy atoms such metal atoms) into the unit cell of the crystal. For a more detailed description of MIR, see U.S. Pat. No. 6,093,573, column 15.

Atomic coordinates refer to Cartesian coordinates (x, y, and z positions) derived from mathematical equations involving Fourier synthesis of data derived from patterns obtained via diffraction of a monochromatic beam of x-rays by the atoms (scattering centers) of biological macromolecule of interest in crystal form. Diffraction data are used to calculate electron density maps of repeating units in the crystal (unit cell). Electron density maps are used to establish the positions (atomic coordinates) of individual atoms within a crystal's unit cell. The absolute values of atomic coordinates convey spatial relationships between atoms because the absolute values ascribed to atomic coordinates can be changed by rotational and/or translational movement along x, y, and/or z axes, together or separately, while maintaining the same relative spatial relationships among atoms. Thus, a biological macromolecule (e.g., a protein) whose set of absolute atomic coordinate values can be rotationally or translationally adjusted to coincide with a set of prior determined values from an analysis of another sample is considered to have the same atomic coordinates as those obtained from the other sample.

Further details on x-ray crystallography can be obtained from U.S. Pat. No. 6,093,573 and International Application Nos. PCT/US99/18441, PCT/US99/11913, and PCT/US00/

03745. The disclosures of all four of these patent documents are incorporated herein by reference in their entirety.

NMR Spectroscopy

While x-ray crystallography requires single crystals of a macromolecule of interest, NMR measurements are carried out in solution under near physiological conditions. However, NMR-derived structures are not as detailed as crystal-derived structures.

While the use of NMR spectroscopy was until relatively recently limited to the elucidation of the 3-D structure of relatively small molecules (e.g., proteins of 100-150 amino acid residues), recent advances including isotopic labeling of the molecule of interest and transverse relaxation-optimized spectroscopy (TROSY) have allowed the methodology to be extended to the analysis of much larger molecules, e.g., proteins with a molecular weight of 110 kDa [Wider (2000) BioTechniques, 29:1278-1294, the disclosure of which is incorporated herein by reference in its entirety].

NMR uses radio-frequency radiation to examine the environment of magnetic atomic nuclei in a homogeneous magnetic field pulsed with a specific radio frequency. The pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space. Protein structures can be determined by performing a number of two- (and sometimes 3- or 4-) dimensional NMR experiments and using the resulting information as constraints in a series of protein folding simulations.

More information on NMR spectroscopy including detailed descriptions of how raw data obtained from an NMR experiment can be used to determine the 3-D structure of a macromolecule can be found in: Protein NMR Spectroscopy, Principles and Practice, J. Cavanagh et al., Academic Press, San Diego, 1996; Gronenborn et al. (1990) Anal. Chem. 62(1):2-15; and Wider (2000), supra. The disclosures of all three of these articles are incorporated herein by reference in their entirety Any available method can be used to construct a 3-D model of a B7-H1 external region of interest from the x-ray crystallographic and/or NMR data, by for example, using a computer as described below. Such a model can be constructed from analytical data points inputted into the computer by an input device and by means of a processor using known software packages, e.g., HKL™, MOSFILM™, XDS™, CCP4™, SHARP™, PHASES™, HEAVY™, XPLOR™, TNT™, NMRCOMPASS™, NMRPIPE™, DIANA™, NMRDRAW™, FELIX™, VNMR™, MADIGRAS™, QUANTA™, BUSTER™, SOLVE™, O™, FRODO™, or CHAIN™. The model constructed from these data can be visualized via an output device of a computer, using available systems, e.g., SILICON GRAPHICS®, EVANS AND SUTHERLAND™, SUN™, HEWLETT PACKARD™, APPLE MACINTOSH™, DEC™, IBM™, or COMPAQ™.

Use of a Computer to Deduce 3-D Structure

The determination of the 3-D structure of B7-H1 or a fragment of B7-H1 can be implemented using computer hardware or software, or a combination of both. However, the determination is preferably implemented in one or more computer programs executing on one or more programmable computers, each containing a processor and at least one input device. The computers will preferably also contain a data storage system (including volatile and non-volatile memory and/or storage elements) and at least one output device. Program code is applied to input data to perform the functions described above and generate output information. The output information is applied to one or more output devices in a known fashion. The computer can be, for example, a personal computer, microcomputer, or work station of conventional design.

Each program is preferably implemented in a high level procedural or object oriented programming language to communicate with a computer system. However, the programs can be implemented in assembly or machine language, if desired. In any case, the language can be a compiled or interpreted language.

Each computer program is preferably stored on a storage media or device (e.g., ROM or magnetic diskette) readable by a general or special purpose programmable computer. The computer program serves to configure and operate the computer to perform the procedures described herein when the program is read by the computer. The method of the invention can also be implemented by means of a computer-readable storage medium, configured with a computer program, where the storage medium so configured causes a computer to operate in a specific and predefined manner to perform the functions described herein.

For example, the computer-requiring steps in the method of the invention can minimally involve:

(a) inputting into an input device, e.g., through a keyboard, a diskette, or a tape, data that can be used to determine the 3-D structure of the B7-H1 molecule or B7-H1 fragment, e.g., a criteria data set containing 3-D atomic co-ordinates of the molecule or fragment; and (b) determining, using a processor, the 3-D structure of the molecule or fragment.

The method can involve the additional step of outputting to an output device a model of the 3-D structure of the molecule or fragment. In addition, the data can be compared to a computer database of, for example, 3-D structures stored in a data storage system.

B7-H1 molecules or B7-H1 fragments to be used for the above 3-D analyses can be purified from natural sources (e.g., from any cell that expresses B7-H1 or can be induced to express it). Smaller peptides (fewer than 100 amino acids long) can be conveniently synthesized by standard chemical means known to those in the art.

In addition, both polypeptides and peptides can be manufactured by standard in vitro recombinant DNA techniques and in vivo transgenesis using nucleotide sequences encoding the appropriate polypeptides or peptides. Methods well-known to those skilled in the art can be used to construct expression vectors containing relevant coding sequences and appropriate transcriptional/translational control signals. See, for example, the techniques described in Sambrook et al., *Molecular Cloning: A Laboratory Manual* (2nd Ed.) [Cold Spring Harbor Laboratory, N.Y., 1989], and Ausubel et al., *Current Protocols in Molecular Biology* [Green Publishing Associates and Wiley Interscience, N.Y., 1989], the disclosures of which are incorporated herein by reference in their entirety Expression systems that may be used for purposes of the invention include but are not limited to microorganisms such as bacteria (for example, *E. coli* and *B. subtilis*) transformed with recombinant bacteriophage DNA, plasmid DNA, or cosmid DNA expression vectors containing nucleic acid (e.g., cDNA) sequences encoding B7-H1 or a fragment of B7-H1; yeast (for example, Saccharomyces and Pichia) transformed with recombinant yeast expression vectors containing nucleic acid (e.g., cDNA) sequences encoding B7-H1 or a fragment of B7-H1; insect cell systems infected with recombinant virus expression vectors (for example, baculovirus) containing nucleic acid (e.g., cDNA) sequences encoding B7-H1 or a fragment of B7-H1; plant cell systems infected with recombinant virus expression vectors (for example, cauliflower mosaic virus (CaMV) or tobacco mosaic virus (TMV)) or transformed with recombinant plasmid expression vectors (for example, Ti plasmid) containing nucleic acid (e.g., cDNA) sequences encoding B7-H1 or a fragment of B7-H1; or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter). Also useful as host cells are primary or secondary cells obtained directly from a mammal and transfected with a plasmid vector or infected with a viral vector.

In the expression vectors mentioned above, nucleic acid (e.g., cDNA) sequences encoding B7-H1 or a fragment of B7-H1 will be operably linked to one or more transcriptional/translation regulatory elements. As used herein, an expression control sequence (transcriptional/translational regulatory element) that is "operably linked" to a coding sequence is incorporated into a genetic construct so it effectively controls expression of the coding sequence. The transcriptional/translational regulatory elements include but are not limited to inducible and non-inducible promoters, enhancers, operators and other elements that are known to those skilled in the art and that drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

Cells transfected or transduced with the expression vectors of the invention can then be used, for example, for large or small scale in vitro manufacture of a B7-H1 molecule or fragment by methods known in the art. In essence, such methods involve culturing the cells under conditions that maximize production of the polypeptide and isolating the polypeptide from the cells or from the culture medium.

For the methods of the invention, it is generally required that the B7-H1 molecules or B7-H1 fragments be highly purified. Methods for purifying biological macromolecules (e.g., proteins) are known in the art. The degree of purity of a B7-H1 molecule or fragment can be measured by any appropriate method, e.g., column chromatography, polyacrylamide gel electrophoresis, or HPLC analysis.

Once the 3-D structure of a B7-H1 external region of interest has been established using any of the above methods, a compound that has substantially the same 3-D structure (or contains a domain that has substantially the same structure) as the relevant B7-H1 external region can be made. In this context, "has substantially the same 3-D structure" means that the compound includes one or more (e.g., one, two, three, four, five, six, seven, eight, nine, ten, 12, 15, 20, 30, 40, 50, 100, or more) epitopes with the ability to bind to an antibody that binds to the B7-H1 external region. One of skill in the art would know how to test a compound for such an ability.

With the above described 3-D structural data on hand and knowing the amino acid sequence of the B7-H1 external region, those of skill in the art would know how to make compounds with the above-described properties. The compounds include any molecules with the ability to inhibit the binding of B7-H1 to a B7-H1-specific antibody. Thus the compounds can be, for example, polypeptides, non-polypeptide molecules, or molecules that are part polypeptide and part non-polypeptide. The compounds can also be small molecules. Methods to make the compounds include standard chemical synthetic methods and, in the case of proteins, recombinant methods (see above). For example, cysteine residues appropriately placed in a compound so as to form disulfide bonds can be used to constrain the compound or a domain of the compound in an appropriate 3-D structure. In addition, one of skill in the art would know what amino acids to include and in what sequence to include them in order to generate, for example, α-helices, β structures, or sharp turns or bends in the polypeptide backbone.

While not essential, computer-based methods can be used to design the compounds of the invention. Appropriate computer programs include: LUDI™ (Biosym Technologies, Inc., San Diego, Calif.), ALADDIN™ (Daylight Chemical Information Systems, Irvine, Calif.); and LEGEND™ [Nishibata et al. (1985) J. Med. Chem. 36(20):2921-2928, the disclosure of which is incorporated herein by reference in its entirety].

These compounds can include, in addition, to the above described immunogenic domains, one or more domains that facilitate purification (e.g., poly-histidine sequences) or domains that serve to direct the compound to organs of the immune system, e.g., ligands or antibodies (including antibody fragments such Fab, F(ab')$_2$, or single chain Fv fragments) specific for cell surface components of cells of the immune system, e.g., the Flt3 ligand or antibodies specific for CD4, CD8, CD3, CD2, CD19, or CD20. Other useful domains include immune stimulatory cytokines (e.g., without limitation, interleukin (IL)-2, IL-4, IL-5, IL-6, IL-10, IL-13), adjuvant molecules (e.g., cholera toxin or E. coli heat labile toxin) or functional fragments of such molecules, i.e., those retaining at least some, e.g., 10%, 20%, 30%, 40%, 50%, 60%, 70%, 80%, 90%, or all, of the activity of the parent molecule, or at least the receptor-binding activity. All that is required in such multidomain compounds is that the immunogenic domain retains the 3-D structure it would have in the absence of the additional domains. Conjugation to make such multidomain compounds can be by chemical methods (e.g., Barrios et al. (1992) Eur. J. Immunol. 22:1365-1372, the disclosure of which is incorporated herein by reference in its entirety]. Where the compound is a peptide, it can be produced as part of a recombinant protein, such as one that self-assembles into virus-sized particles (e.g., U.S. Pat. No. 4,918,166, the disclosure of which is incorporated herein by reference in its entirety) that display the immunogenic peptide on the surface.

Compounds of the invention that are peptides also include those described above, but modified for in vivo use by the addition, at the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptide compounds can be covalently or noncovalently coupled to pharmaceutically acceptable "carrier" proteins prior to administration.

Also of interest are peptidomimetic compounds that are designed based upon the amino acid sequences of compounds of the invention that are peptides. Peptidomimetic compounds are synthetic compounds having a three-dimensional conformation (i.e., a "peptide motif") that is substantially the same as the three-dimensional conformation of a selected peptide. The peptide motif provides the peptidomimetic compound with the ability to elicit the production of antibodies cross-reactive with a selected peptide. Peptidomimetic compounds can have additional characteristics that enhance their in vivo utility, such as increased cell permeability and prolonged biological half-life.

The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

Methods of Inhibiting Binding of B7-H1-specific Antibodies to B7-H1

These methods of the invention involve inhibiting binding of agonist B7-H1-specific antibodies to T cells in order to prevent costimulation and hence activation of the T cells. In these methods, one or more (a) compounds that either compete with B7-H1 for binding to a B7-H1-specific antibody or (b) non-agonist compounds that bind to B7-H1 (and thus inhibit binding of a B7-H1-specific antibody to B7-H1 on a T cell) can be delivered to the environment of T cells of interest. Compounds in category (a) include any of the B7-H1 reagents listed above as well as compounds identified by the methods described above. Compounds in category (b) include non-agonist antibodies or antibody fragments specific for B7-H1. Non-agonist antibody fragments include monovalent antibody fragments such as Fab or single chain Fv (scFV) antibody fragments as well as polyvalent (e.g., divalent) fragments (such as F(ab')$_2$ fragments) without intact Fc regions through which non-specific binding to Fc receptors on cells occurs. An scFv fragment is a single polypeptide chain that includes both the heavy and light chain variable regions of the antibody from which the scFv is derived. One of skill in the art will also know how to test whether an intact antibody is non-agonist antibody. It is likely, for example, that IgM antibodies will be non-agonist antibodies.

All the antibodies described herein can be polyclonal antibodies or mAb and can be from any of a wide range of species, e.g., a human, a non-human primate (e.g., a monkey or a chimpanzee), a cow, a horse, a goat, a sheep, a pig, a cat, a dog, a rabbit, a guinea pig, a hamster, a gerbil, a rat, a mouse, or a chicken. Also included are chimeric antibodies, e.g., humanized antibodies.

Antibody fragments that contain the binding domain of an antibody molecule can be generated by known techniques. For example: F(ab')$_2$ fragments can be produced by pepsin digestion of antibody molecules; and Fab fragments can be generated by reducing the disulfide bridges of F(ab')$_2$ fragments or by treating antibody molecules with papain and a reducing agent. See, e.g., National Institutes of Health, 1 *Current Protocols In Immunology*, Coligan et al., ed. 2.8, 2.10 (Wiley Interscience, 1991), the disclosure of which is incorporated herein by reference in its entirety. scFv fragments can be produced, for example, as described in U.S. Pat. No. 4,642,334, which is incorporated herein by reference in its entirety.

Chimeric and humanized monoclonal antibodies can be produced by recombinant DNA techniques known in the art, for example, using methods described in Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., U.S. Pat. No. 4,816,567; Cabilly et al., European Patent Application 125,023; Better et al. (1988) Science 240, 1041-43; Liu et al. (1987) J. Immunol. 139, 3521-26; Sun et al. (1987) PNAS 84, 214-18; Nishimura et al. (1987) Canc. Res. 47, 999-1005; Wood et al. (1985) Nature 314, 446-49; Shaw et al. (1988) J. Natl. Cancer Inst. 80, 1553-59; Morrison, (1985) Science 229, 1202-07; Oi et al. (1986) BioTechniques 4, 214; Winter, U.S. Pat. No. 5,225,539; Jones et al. (1986) Nature 321, 552-25; Veroeyan et al. (1988) Science 239, 1534; and Beidler et al. (1988) J. Immunol. 141, 4053-60. The disclosures of all these articles and patent documents are incorporated herein by reference in their entirety.

Fully human antibodies (polyclonal or monoclonal) can be produced by immunizing transgenic animals (e.g., mice) that contain gene segments encoding gene segments encoding all human immunoglobulin (i.e., variable, joining, diversity, and constant) regions (see, for example, U.S. Pat. Nos. 5,545,806 and 5,569,825).

The methods of inhibiting activation of a cell can be in vitro, in vivo, or ex vivo.

In vitro application of the methods of the invention can be useful in basic scientific studies of, for example, T cell costimulation and biology. In the in vitro methods of the invention, the compounds can be cultured with T cells (CD4+ and/or CD8+) or cell populations containing T cells (e.g., peripheral blood mononuclear cell, spleen cells, or lymph node cells), one or more agonist B7-H1-specific antibodies, and a T cell receptor (TCR) ligating agent (e.g., antigen and antigen presenting cells (APC), antigen-pulsed APC, antigen-expressing APC, or an immobilized anti-TCR or anti-CD3 antibody). Measurements of the level of T cell proliferation/survival, T cell apoptosis, or T cell function (e.g., cytotoxicity or cytokine production) can be made after various times of culture using well-established methods. It is clear that these in vitro methods can be adapted as screening assays to test compounds for their ability to inhibit binding of a B7-H1-specific antibody to B7-H1. Moreover, a compound known to inhibit binding of a B7-H1-specific antibody to B7-H1 can also be a "positive control" in such screening assays.

The methods of the invention are preferably in vivo or ex vivo. These applications can be useful in the therapy and prophylaxis of any of the activated T cell-mediated diseases or pathological conditions mentioned above. Optionally, a first step in the in vivo and ex vivo methods can be identifying the subject as having an elevated level in a body fluid (e.g., blood) of one more antibodies that bind to B7-H1.

As used herein, "prophylaxis" can mean complete prevention of the symptoms of a disease, a delay in onset of the symptoms of a disease, or a lessening in the severity of subsequently developed disease symptoms. "Prevention" means that symptoms of the disease are essentially absent. As used herein, "therapy" can mean a complete abolishment of the symptoms of a disease or a decrease in the severity of the symptoms of the disease.

Modifications of the above-described in vivo methods of the invention can be used as screening assays for compounds that are effective prophylactic and/or therapeutic agents against a disease or pathological condition of interest. In such a method, a test compound that inhibits the binding of a B7-H1-specific antibody to B7-H1 can be administered to a test subject (e.g., an experimental animal or a human patient) before or after onset of disease or pathological condition symptoms. Where appopriate, some stimulus (e.g., an antigen or allergen) can be administered to the subject before simultaneous with, or after administration of the compound.

A determination of the efficacy of the compound is then made by, for example, detecting or measuring a reduction in one or more symptoms (e.g., fever, rash, sneezing, difficulty in breathing, or limb or digit stiffness) of the disease or pathological condition can be detected or measured.

The methods of the invention can be applied to a wide range of species, e.g., humans, non-human primates, horses, cattle, pigs, sheep, goats, dogs, cats, rabbits, guinea pigs, hamsters, rats, gerbils, and mice.

In Vivo Approaches

In a preferred in vivo approach, the isolated compound itself is administered to the subject. Generally, the compounds will be suspended in a pharmaceutically-acceptable carrier (e.g., physiological saline) and administered orally or by intravenous (i.v.) infusion, or injected subcutaneously, intramuscularly, intrathecally, intraperitoneally, intrarectally, intravaginally, intranasally, intragastrically, intratracheally, or intrapulmonarily. They can, for example, be delivered directly to a site of an immune response. e.g., a lymph node in the region of an affected tissue or organ or spleen. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001-100.0 mg/kg. Wide variations in the needed dosage are to be expected in view of the variety of compounds available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more fold). Encapsulation of the compound in a suitable delivery vehicle (e.g., polymeric microparticles or implantable devices) may increase the efficiency of delivery, particularly for oral delivery.

Alternatively, where an inhibitory compound is a polypeptide, a polynucleotide containing a nucleic acid sequence encoding the polypeptide can be delivered to appropriate cells in a mammal. Expression of the coding sequence can be directed to any cell in the body of the subject. However, expression will preferably be directed to cells in, or close to, lymphoid tissue draining an affected tissue or organ. Expression of the coding sequence can be directed to T cell or other immune-related cells, e.g., B cells, macrophages/monocytes, or interdigitating dendritic cells. This can be achieved by, for example, the use of polymeric, biodegradable microparticle or microcapsule delivery devices known in the art and/or tissue or cell-specific antibodies.

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), J. Mol. Med. 73:479]. Alternatively, tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

In the relevant polynucleotides (e.g., expression vectors), the nucleic acid sequence encoding the polypeptide of interest with an initiator methionine and optionally a targeting sequence is operatively linked to a promoter or enhancer-promoter combination. Short amino acid sequences can act as signals to direct proteins to specific intracellular compartments. Such signal sequences are described in detail in U.S. Pat. No. 5,827,516, the disclosure of which is incorporated herein by reference in its entirety.

Enhancers provide expression specificity in terms of time, location, and level. Unlike a promoter, an enhancer can function when located at variable distances from the transcription initiation site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. The coding sequence of the expression vector is operatively linked to a transcription terminating region.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., decreased proliferation of cancer cells) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to approximately $10^{12}$ copies of the polynucleotide molecule. This dose can be repeatedly administered, as needed. Routes of administration can be any of those listed above.

Ex Vivo Approaches

An ex vivo strategy can involve transfecting or transducing cells obtained from the subject with a polynucleotide encoding a protein than inhibits binding of an agonist B7-H1-specific antibody to B7-H1 on a T cell (see above). The transfected or transduced cells are then returned to the subject. The cells can be any of a wide range of types including, without limitation, hemopoietic cells (e.g., bone marrow cells, macrophages, monocytes, interdigitating dendritic cells, T cells, or B cells), fibroblasts, epithelial cells, endothelial cells, keratinocytes, or muscle cells. Such cells act as a source of the inhibitory polypeptide for as long as they survive in the subject. The cells, optionally treated with an agent (e.g., ionizing irradiation) that ablates their proliferative capacity, are then introduced into the patient, where they secrete the polypeptide.

The ex vivo methods include the steps of harvesting cells from a subject, culturing the cells, transducing them with an expression vector, and maintaining the cells under conditions suitable for expression of the polypeptide that inhibits binding of an agonist B7-H1-specific antibody to B7-H1 on a T cell. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced can then be selected, for example, for expression of the coding sequence or of a drug resistance gene. The cells may then be lethally irradiated (if desired) and injected or implanted into the patient.

Methods of Inhibiting Expression of B7-H1 in a T Cell

Also included in the invention are methods of inhibiting expression of B7-H1 in T cells. One such method involves introducing into a T cell (a) an antisense oligonucleotide or (b) a nucleic acid comprising a transcriptional regulatory element (TRE) operably linked to a nucleic sequence that is transcribed in the T cell into an antisense RNA. The antisense oligonucleotide and the antisense RNA hybridize to an B7-H1 transcript and have the effect in the T cell of inhibiting expression of B7-H1. Inhibiting B7-H1 expression in the cell can inhibit activation of the T cell by anti-B7-H1 antibodies and thus the method can be useful in the treatment and/or prophylaxis of any of the activated T cell-mediated diseases and pathological conditions recited herein. The method can be used, for example, in the treatment of RA.

Antisense compounds are generally used to interfere with protein expression either by, for example, interfering directly with translation of a target mRNA molecule, by RNAse-H-mediated degradation of the target mRNA, by interference with 5' capping of mRNA, by prevention of translation factor binding to the target mRNA by masking of the 5' cap, or by inhibiting of mRNA polyadenylation. The interference with protein expression arises from the hybridization of the antisense compound with its target mRNA. A specific targeting site on a target mRNA of interest for interaction with an antisense compound is chosen. Thus, for example, for modulation of polyadenylation, a preferred target site on an mRNA target is a polyadenylation signal or a polyadenylation site. For diminishing mRNA stability or degradation, destabilizing sequence are preferred target sites. Once one or more target sites have been identified, oligonucleotides are chosen which are sufficiently complementary to the target site (i.e., hybridize sufficiently well under physiological conditions and with sufficient specificity) to give the desired effect.

With respect to this invention, the term "oligonucleotide" refers to an oligomer or polymer of RNA, DNA, or a mimetic of either. The term includes oligonucleotides composed of naturally-occurring nucleobases, sugars, and covalent internucleoside (backbone) linkages. The normal linkage or backbone of RNA and DNA is a 3' to 5' phosphodiester bond. The term also refers however to oligonucleotides composed entirely of, or having portions containing, non-naturally occurring components which function in a similar manner to the oligonucleotides containing only naturally-occurring components. Such modified substituted oligonucleotides are often preferred over native forms because of desirable properties such as, for example, enhanced cellular uptake, enhanced affinity for target sequence, and increased stability in the presence of nucleases. In the mimetics, the core base (pyrimidine or purine) structure is generally preserved but (1) the sugars are either modified or replaced with other components and/or (2) the inter-nucleobase linkages are modified. One class of nucleic acid mimetic that has proven to be very useful is referred to as protein nucleic acid (PNA). In PNA molecules the sugar backbone is replaced with an amide-containing backbone, in particular an aminoethylglycine backbone. The bases are retained and are bound directly to the aza nitrogen atoms of the amide portion of the backbone. PNA and other mimetics useful in the instant invention are described in detail in U.S. Pat. No. 6,210,289, the disclosure of which is incorporated herein by reference in its entirety.

The antisense oligomers to be used in the methods of the invention generally comprise about 8 to about 100 (e.g., about 14 to about 80 or about 14 to about 35) nucleobases (or nucleosides where the nucleobases are naturally occurring).

The antisense oligonucleotides can themselves be introduced into a cell or an expression vector containing a nucleic sequence (operably linked to a TRE) encoding the antisense oligonucleotide can be introduced into the cell. In the latter case, the oligonucleotide produced by the expression vector is an RNA oligonucleotide and the RNA oligonucleotide will be composed entirely of naturally occurring components.

The methods of the invention can be in vitro or in vivo. In such in vitro methods, T cells, can be incubated for various lengths of time with (a) the antisense oligonucleotides or (b) expression vectors containing nucleic acid sequences encoding the antisense oligonucleotides at a variety of concentrations. Other incubation conditions known to those in art (e.g., temperature or cell concentration) can also be varied. Inhibition of B7-H1 expression can be tested by methods known to those in the art, e.g., methods such as those disclosed herein. In vitro methods can be used for basic scientific studies on gene expression and/or mechanisms of T cell activation or costimulation. They can also be adapted to screen for candidate anti-sense oligonucleotides for their ability to inhibit expression of B7-H1 in a T cell; moreover, the method per se can be used as a "positive control" in such screening assays.

The methods will preferably be in vivo.

Where antisense oligonucleotides per se are administered, they can be suspended in a pharmaceutically-acceptable carrier (e.g., physiological saline) and administered under the same conditions described above for compounds that inhibit binding of an agonist B7-H1-specific antibody to B7-H1.

Where an expression vector containing a nucleic sequence (operably linked to a TRE) encoding the antisense oligonucleotide is administered to a subject, expression of the coding sequence can be directed to a T cell in the body of the subject using any of the cell- or tissue-targeting techniques described above for vectors that express polypeptides that inhibit binding of an agonist B7-H1-specific antibody to B7-H1.

Double-stranded interfering RNA (RNAi) homologous to B7-H1 DNA can also be used to reduce expression of B7-H1 in T cells. See, e.g., Fire et al. (1998) Nature 391:806-811; Romano and Masino (1992) Mol. Microbiol. 6:3343-3353; Cogoni et al. (1996) EMBO J. 15:3153-3163; Cogoni and Masino (1999) Nature 399:166-169; Misquitta and Paterson (1999) Proc. Natl. Acad. Sci. USA 96:1451-1456; and Kennerdell and Carthew (1998) Cell 95:1017-1026. The disclosures of all these articles are incorporated herein by reference in their entirety.

The sense and anti-sense RNA strands of RNAi can be individually constructed using chemical synthesis and enzymatic ligation reactions using procedures known in the art. For example, each strand can be chemically synthesized using naturally occurring nucleotides or variously modified nucleotides designed to increase the biological stability of the molecule or to increase the physical stability of the duplex formed between the sense and anti-sense strands, e.g., phosphorothioate derivatives and acridine substituted nucleotides. The sense or anti-sense strand can also be produced biologically using an expression vector into which a target B7-H1 sequence (full-length or a fragment) has been subcloned in a sense or anti-sense orientation. The sense and anti-sense RNA strands can be annealed in vitro before delivery of the dsRNA to any of cancer cells disclosed herein. Alternatively, annealing can occur in vivo after the sense and anti-sense strands are sequentially delivered to the T cells.

Double-stranded RNAi interference can also be achieved by introducing into T cells a polynucleotide from which sense and anti-sense RNAs can be transcribed under the direction of separate promoters, or a single RNA molecule containing both sense and anti-sense sequences can be transcribed under the direction of a single promoter.

It will be understood that certain drugs and small molecules can also be used inhibit expression of B7-H1 in T cells.

One of skill in the art will appreciate that RNAi, drug, and small molecule methods can be, as for the antisense methods described above, in vitro and in vivo. Moreover, methods and conditions of delivery are the same as those for antisense oligonucleotides.

The antisense, RNAi, drug, and small molecule methods of the invention can be applied to a wide range of species, e.g., humans, non-human primates, horses, cattle, pigs, sheep, goats, dogs, cats, rabbits, guinea pigs, hamsters, rats, gerbils, and mice.

In any of the above in vitro, in vivo, and ex vivo methods of inhibiting binding of a B7-H1-specific antibody to B7-H1 and of inhibiting expression of B7-H1 in a T cell, one or more (e.g., two, three, four, five, six, seven, eight, nine, ten, 11, 12, 15, 18, 20, 25, 30, 40, 50, 60, 70, 80, 100, or more) inhibitory compounds, antisense oligonucleotides, RNAi, drugs, or small molecules (or vectors encoding them) can be used. Moreover, they can be used together with one or more (e.g., two, three, four, five, six, seven, eight, nine, ten, 11, 12, 15, 18, 20, 25, 30, 40, 50, 60, 70, 80, 100, or more) supplementary agents. Such supplementary agents include substances that serve, for example, to inhibit infection (e.g., standard antimicrobial antibiotics), inhibit activation of T cells, or inhibit the consequences of T cell activation, e.g., immunoregulatory cytokines or antibodies specific for such cytokines. For example, where it is desired to decrease a Th1-type immune response (e.g., in a DTH response), a cytokine such as interleukin (IL)-4, IL-10, or IL-13 or an antibody specific for a cytokine such as IL-12 or interferon-γ (IFN-γ) can be used as a supplementary agent. Alternatively, where it is desired to inhibit a Th2-type immune response (e.g., in an immediate type hypersensitivity response), a cytokine such as IL-12 or IFN-γ or an antibody specific for IL-4, IL-10, or IL-13 can be used as a supplementary agent. Also of interest as supplementary agents are antibodies (or any of the above-described antibody fragments or derivatives) specific for proinflammatory cytokines and chemokines such as IL-1, IL-6, IL-8, tumor necrosis factor-α (TNF-α), macrophage inflammatory protein (MIP)-1, MIP-3α, monocyte chemoattractant protein-1 (MCP-1), epithelial neutrophil activating peptide-78 (ENA-78), interferon-γ-inducible protein-10 (IP10), Rantes, and any other appropriate cytokine or chemokine recited herein.

The following examples are meant to illustrate, not limit, the invention.

EXAMPLES

Example 1

Materials and Methods

Patients and Healthy Donors

Serum samples were obtained from 63 patients with diagnosed RA autoinimune disease and 54 sex- and age-matched healthy donors under the approval of the Internal Review Board of the Mayo Clinic. Diagnosis of RA was defined according to the classification criteria of the American College of Rheumatology. Sera or plasma samples were collected from the 63 RA patients (53 women and 10 men, mean age, 58 years; age range, 17-80 years) and 54 health donors (42 women and 12 men, mean age, 52; age range 20-69). Human IgG was purified by IMMUNOPURE (G)™ IgG purification kits (Pierce, Rockford, Ill.).

Enzyme-linked Immunosorbent Assay (ELISA)

A purified fusion protein consisting of the extracellular domain of human B7-H1 (hB7-H1) fused to the CH2 and CH3 domains of mouse IgG2a (B7-H1Ig) or control mouse IgG2a (mIgG2a) was coated (at a concentration of 2 µg/ml in PBS (phosphate-buffered saline)) overnight onto ELISA plate wells at 4° C. The wells were then blocked with PBS containing 10% fetal bovine serum (FBS). Sera from healthy donors or RA patients were diluted in PBS at 1:1000 in triplicate before adding to the plates. After reaction, the wells were washed 6 times in PBS containing 0.1% Tween-20. Bound antibodies were detected by incubation with a horseradish peroxidase (HRPO)-conjugated goat anti-human IgG antibody (Biosource, Camarillo, Calif.) at a 1/2,000 dilution for 1.5 hours at room temperature. Unbound HRPO-conjugated antibody was washed out of the wells, TMB (tetramethylbenzidine) was added to the wells, and the $OD_{450}$ of all the wells was measured using a multi-microplate reader. Nonspecific binding of sera to plates coated with control Ig (mouse IgG2a) was subtracted from each sample.

Generation of mAbs Specific for B7-H1

BALB/c mice were immunized with purified B7-H1Ig mixed with complete Freund's adjuvant (Sigma, St. Louis, Mo.) and boosted three times with B7-H1Ig in incomplete Freund's adjuvant. Sera from the mice were collected and their specific binding to hB7-H1 was determined by ELISA and fluorescence flow cytometry (FFC) analysis of 293 cells transfected with and expressing cDNA encoding hB7-H1 (B7-H1/293 cells) [Dong et al. (1999) Nature Med. 5:1365-1369]. Spleen cells from mice with the highest titer of hB7-H 1-specific antibody in their sera were fused with SP2/0 myeloma cells to produce hybridoma cells using standard techniques. After several rounds of selection by ELISA and FFC, 2 clones (2H1 and 5H1) producing antibody which consistently stained B7-H1/293 cells were obtained. The isotype of both 2H1 and 5H1 is IgG1. Culture supernatants of the 2H1 and 5H1 hybridomas were concentrated and purified by with PROTEIN G-SEPHAROSE™ columns (Pierce, Rockford, Ill.) and dialyzed in LPS (lipopolysaccharide)-free PBS. In some experiments, polymyxin B was incorporated in the assays of cell proliferation and cytokine secretion to neutralize residual LPS.

T Cell Activation and Fluorescence Flow Cytometry (FFC) Analysis

Freshly isolated human peripheral blood mononuclear cells (PBMC; $1 \times 10^7$ cells/ml) were stimulated with 5 µg/ml of PHA (phytohemagglutinin; Sigma) for various lengths of time. The cells were harvested and analyzed by FFC after 0, 24 and 48 hours of treatment. For direct immunofluorescence staining, T cells were incubated at 40° C. with 1 μg of FITC- or PE- conjugated mAb for 30 minutes and analyzed by FFC using a FACSCAN™ flow cytometer (Becton Dickinson, Mountain View, Calif.) with Cell Quest software (Becton Dickinson) as described previously [Dong et al. (1999)]. mAb specific for CD4 (RPA-T4), CD8 (RPA-T8), CD45RO (UCHL1) were purchased from BD-PharMingen (San Diego, Calif.) and rabbit anti-human TRAIL polyclonal antibody was purchased from Alexis Biochemicals (San Diego, Calif.). For indirect immunofluorescence staining, cells were first incubated with B7-H1- specific mAb (3 μg/sample) at 40° C. for 30 minutes. The cells were washed and further incubated with FITC (fluorescein isothiocyanate)- (Biosource, Camarillo, Calif.) or PE (phycoerythrin)-(Southern Biotechnology Associates, Inc., Birmingham, Ala.) conjugated goat anti-mouse IgG F(ab') 2 for 30 minutes at 40° C. Mouse IgG1 (Sigma) was used as control Ig in the indirect staining experiments. In some experiments, cells were treated with human Ig before incubation with FITC- or PE-conjugated mAbs to prevent non-specific binding of antibodies via Fc receptors on the cells.

Costimulation of T Cell Responses

Purified human CD4+ T cells were cultured ($2 \times 10^5$ cells/well in triplicate) in the wells of 96-well flat-bottomed microtiter tissue culture plates that were pre-coated overnight with anti-human CD3 mAb (HIT3a, BD-PharMingen, Palo Alto, Calif.) in the presence of hB7-H1-specific mAbs, PD-1Ig, or control Ab (mouse IgG1). PD-1Ig is a fusion protein containing the extracellular domain of PD1 fused to the CH2 and CH3 domains of mouse IgG2a. Anti-CD28 mAb (CD28.2, BD-PharMingen) was included as positive control. To block the effect of B7-H1 mAb, soluble B7-H1Ig or control Ig (mIgG2a) was pre-cultured with coated B7-H1 mAb for 30 minutes before addition of CD4+ T cells to the culture wells.

To detect interleukin (IL)-10, supematants were harvested at 24, 48 and 72 hours from the cultures and the concentrations of IL-10 were determined by sandwich ELISA methods (BD- PharMingen) according to manufacturer's instructions. T cell proliferation was determined by the addition of 1.0 μCi $^3$H-TdR ($^3$H-thymidine) 16 hours prior to harvesting of the cultures. Cell proliferation was measured in terms of the amount (in counts per minute; cpm) of $^3$H-TdR incorporated into the cells. Radioactivity was measured by liquid scintillation counting in a MICROBETA TRJLUX™ liquid scintillation counter (Wallac, Finland).

Induction and Analysis of Apoptosis

Purified human CD4+ T cells ($4 \times 10^5$ /ml) were cultured with hB7-H1-specific mAbs or control mAb at 10 μg/ml in the presence of immobilized anti-CD3 mAb (500 ng/ml). At various times after initiation of the cultures, aliquots ($1 \times 10^5$) of the cells were stained by FITC-conjugated annexin V (AV) (PharMingen) at 5 μl/test and propidium iodide (PI) (Sigma) at 5 μg/ml for 1 hour. The samples were analyzed by FFC. For blocking the effect of apoptosis, neutralizing mAbs specific for IL-10 (R&D, Minneapolis, Minn.), IL-2 (MQ-17H12, BD-PharMingen), or Fas ligand (NOK-1, BD-PharMingen) were added at 10 μg/ml at the beginning of culture.

Detection of Apoptosis-Related Gene Expression

Total RNA was prepared using TRI REAGENT™ (Sigma) from 5 ×10 T cells which had been stimulated by anti-CD3/B7-H1 mAb or anti-CD3/control Ab for 24, 48, 72 hours. 10 μg of RNA was used as a template for $^{32}$P cDNA probe synthesis. A human Apoptosis1 GEARRAY™ (SuperArray Inc., Bethesda, Md.) was used to analyze the expression of 23 apoptosis-related genes and two control "house-keeping" genes, i.e., actin and GAPDH genes. Analysis of gene expression using the Apoptosis1 GEARRAY™ was carried out by side-by-side hybridization with the cDNA probes according to the manufacturer's instructions. A STORM™ Phosphoimager system (Molecular Dynamics, Sunnyvale, Calif.) was used to directly quantify the intensity of the signals. The relative abundance of a particular transcript was estimated by comparing its signal intensity to the signal derived from Beta-actin or GAPDH. Data are expressed as fold increase in signal obtained with cDNA derived from T cells that were stimulated with B7-H1 mAb versus control antibody.

Detection of Active Caspase-3

The CASPATAGTM CASPASE-3 (DEVD) ACTIVITY KIT ™ (Intergen, Purchase, NY) was used to detect the activated form of caspase-3 in CD4+ T cells. The kit detects active caspases in living cells by means of a carboxyfluoresein labeled caspase inhibitor (FAM-DEVD-FMK). The inhibitor irreversibly binds to active caspases and the caspase positive cells were detected by FFC according to the manufacturer's instructions. Briefly, 300 μl of $10^6$ cells/ml was added to a fresh test tube and incubated with 10 μl of 30x diluted FAM-DEVD-FMK solution for 1 hour at 37° C under 5% $CO_2$ in the dark. After incubation, the cells were washed twice with 2 ml of 1x wash buffer (supplied by the manufacturer of the kit), re-suspended in 400 μl of 1x wash buffer, and analyzed by FFC.

Example 2

Costimulatory B7-H1 Autoantibodies in RA Serum

To evaluate the potential role of autoantibodies in prolonged activation of T cells in RA, IgG samples purified from the sera of RA patients were tested for their ability to regulate the proliferation of T cells in vitro. In the presence of suboptimal doses (30-50 ng/ml) of anti-CD3 monoclonal antibody (mAb) (to mimic TCR-mediated signaling), IgG purified from the sera of two RA patients, but not control IgG, coated onto the bottoms of culture wells, significantly enhanced the in vitro proliferation of purified CD4+ T cells in a dose-dependent fashion (FIG. 1A). In the absence of anti-CD3 mAb, purified IgG from RA patients had no such effect (data not shown). Soluble IgG (i.e., not coated onto culture well bottoms but added to the culture medium containing the cells) from these RA patients did not have this activity (FIG. 1B). The costimulatory activity of the autoantibodies was completely blocked by the inclusion of soluble B7-H1Ig fusion protein, but not by PD-1Ig or control IgG (mouse IgG2a), in the cultures (FIG. 1C). These results indicate that costimulatory activity for CD4+ T cells was mediated by autoantibodies specific for hB7-H1 in the sera of the RA patients.

To directly test for the presence of autoantibodies specific for hB7-H1 in the sera of RA patients, sera from 63 RA patients were examined by a specific sandwich ELISA using ELISA plates with well bottoms coated with purified B7-H1Ig. Autoantibodies binding to hB7-H1 were detected by anti-human IgG mAb. The ELISA employed was highly specific for hB7-H1 because binding of patients' sera could be selectively blocked by pre-incubation of sera with soluble B7-H1Ig, but not control mIgG2a (FIG. 1D). An $OD_{450}$ 0.123 (based on the mean (0.057) +/−2× standard deviation (0.033) of the values with sera from 54 healthy donors at 1:1000 dilutions) was used as an arbitrary "cut-off" for positivity. As shown in FIG. 1E, sera from 18 of 63 RA patients (29%) contained significantly elevated levels autoantibodies specific for hB7-H1, while only 4% of 54 healthy donors were marginally positive for the presence of autoantibodies to hB7-H1 (p=0.0002). Similar to the findings of Matsui et al. [(1999) J. Immunol. 162:4328-4335], no autoantibodies to specific for human B7-1 (hB7-1) were detected in the sera of any of the RA patients (FIG. 1F).

Figure 1G:
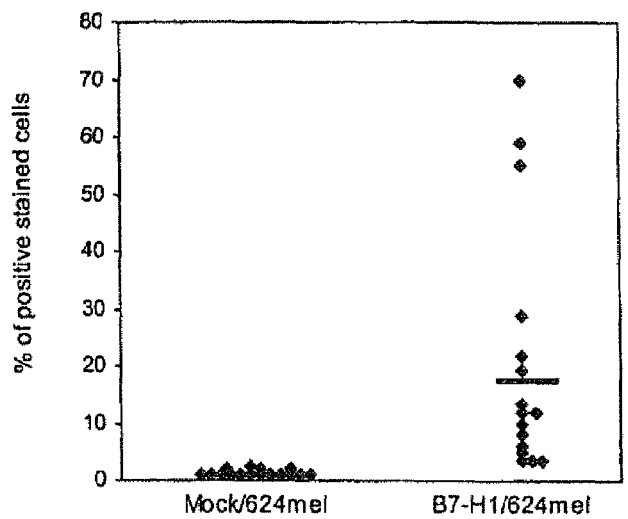
FIG. 1G is a scatter graph showing the binding of antibodies in sera from 16 RA patients to control mock transfected melanoma cells ("Mock/624mel") and melanoma cells transfected with and expressing cDNA encoding human B7-H1 ("B7-H1/624mel"). The sera from the 16 RA patients had previously been found by ELISA to contain human B7-H1-specific antibodies. The results, which were calculated from fluorescence flow cytometry (FFC) analyses, are expressed as the percent of total cells showing positive staining ("% of positive stained cells"). The horizontal bar shows the average percent of positive staining cells in samples of melanoma cells transfected with and expressing cDNA encoding human B7-H1.

The presence of hB7-H1 autoantibodies was also tested by the binding to 624 melanoma cells transfected with, and expressing, cDNA encoding hB7-H1 (B7-H1/624mel) [Dong et al. (2002) Nature Med. 8:793-800]. A significant fraction of the 16 RA patient sera that were positive in ELISA assay also stained B7-H1/624mel but not mock transfected 624 melanoma cells (Mock/624mel) (FIG. 1G). The specificity of the binding was again confirmed by complete blockade of binding when B7-H1Ig was incubated with the diluted sera prior to testing. In addition, all the samples that were negative in ELISA for the presence of autoantibodies to hB7-H1 also failed to bind to B7-H1/624mel (data not shown). These results indicate that a significant proportion of RA patients has an elevated level of autoantibodies to hB7-H1.

Example 3

Correlation of the Presence of B7-H1-specific Autoantibodies with RA Activity

Figure 1H:
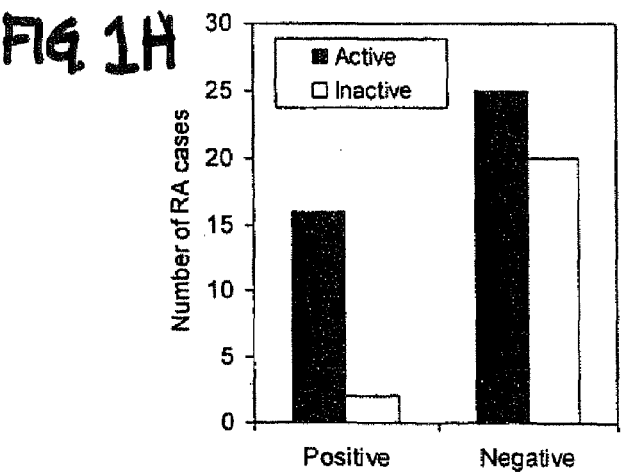
FIG. 1H is bar graph showing the relative number of RA patients ("Number of RA cases") having active disease ("Active"; black bars) and inactive disease ("Inactive"; unfilled bars) in RA patient groups having detectable ("Positive") and undetectable ("Negative") levels of human B7-H1-specific autoantibodies.

A possible relationship between the presence of hB7-H1-specific autoantibodies and RA disease activity was examined. Active disease was defined as the presence of at least nine tender joints, six swollen joints, and one or both of the following: one hour of morning stiffness or elevated Westergren sedimentation rate [Felson et al. (1995) Arthritis Rheum. 38:727-735]. A significant correlation was found between active disease and the presence of hB7-H1-specific autoantibodies in 63 patients with RA. Eighty nine percent of RA patients in the hB7-H1 autoantibody-positive group had active disease, while only 56% of RA patients in the hB7-H1 autoantibody-negative group demonstrated disease activity (P=0.017) (FIG. 1H). These results, combined with those described above, indicate that autoantibodies to B7-H1 may be involved in RA disease progression via a direct effect on T cells.

Example 4

Reverse Costimulation of CD4+ T Cells by mAb Specific for hB7-H1

Autoantibodies from sera are polyvalent with multiple different specificities limiting the potential for functional analysis. To facilitate further study of the effect of B7-H1 autoantibodies on T cell responses, hybridomas that secrete mAb specific for hB7-H1 were generated. Two mAbs (2H1 and 5H1) were found by FFC to specifically bind to hB7-H1 on 293 cells transfected with hB7-H1 coding sequence-containing plasmid (B7-H1/293) but not to mock-transfected 293 cells (Mock/293). In these and other studies, 5H1 and 2H1 were found to have essentially identical features and were used interchangeably.

The ability of 5H1 mAb to block the binding of PD-1Ig to B7-H1/293 cells was tested. As shown in FIG. 2A, PD-1Ig bound to B7-H1/293 cells but not mock/293 cells. Inclusion of 5H1 mAb up to a concentration of 20 µg/ml during staining did not interfere with the binding of PD-1Ig. However, 5H1 mAb could partially block the binding of B7-H1Ig to the M99 T cell clone that expresses a putative non-PD-1 receptor for B7-H1 but not PD-1 [Dong et al. (2002)]. These results indicate that mAb 5H1 selectively blocks B7-H1 binding to a non-PD-1 receptor.

FFC analysis using hB7-H1-specific mAb showed that hB7-H1 is not detectable on freshly isolated peripheral blood mononuclear cells (PBMC) subsets with CD4, CD8 or CD45RO markers. However, stimulation with PHA (a non-specific polyclonal T cell mitogen) rapidly up-regulated expression of hB7-H1 on 64.2% of CD4+ cells at 24 hours and 78.2% at 48 hours (FIG. 2B). Only 44.7% and 32.1% of CD8+ T cells expressed B7-H1 after 24 hr and 48 hours of PHA stimulation, respectively. High levels of hB7-H1 (84.2% at 24 hr and 62.3% at 48 hr) were also detected on CD45RO+ memory T cells. In addition, stimulation of CD4+ T cells with immobilized CD3-specific mAb in optimal doses upregulates the expression of hB7-H1 within 24 hrs while suboptimal doses of CD3-specific mAb requires more than 48 hrs to induce B7-H1 expression (data not shown). Thus it appears that hB7-H1 is inducible on human T cells and is preferentially expressed on activated CD4+ T cells and CD45RO+ memory T cells.

To evaluate the function of T cell-associated B7-H1, human CD4+ T cells were activated with a suboptimal concentration (30 ng/ml) of immobilized anti-CD3 mAb in combination with immobilized hB7-H1-specific mAb. While anti-CD3 mAb alone induced minimal T cell proliferation, significant increases in T cell proliferation were observed by inclusion of hB7-H1 mAb. This effect, however, was less potent than that of anti-CD28 mAb (FIG. 3A). Costimulatory activity was also observed using immobilized human PD-1Ig. The effect of the hB7-H1-specific mAbs was dose-dependent in a range of 2.5 µg/ml ("⅛") to 10 µg/ml ("½") (FIG. 3B). Immobilization of the hB7-H1-specific mAb was critical for the effect since hB7-H1-specific mAb in soluble form in doses up to 20 µg/ml were ineffective (FIG. 3C). TCR signaling was also required for proliferation as hB7-H1-specific mAb did not stimulate T cell proliferation in the absence of anti-CD3 mAb (FIG. 3A). Inclusion of soluble B7-H1Ig, which competitively inhibits the interaction between T cell-associated hB7-H1 and hB7-H1-specific mAb, significantly reduced the costimulatory effect of hB7-H1-specific mAb on T cells (FIG. 3D). In contrast, soluble B7-1Ig (a fusion protein containing the extracellular domain of human B7-1 fused to the CH2 and CH3 domains of mouse IgG2a) or control Ig had no inhibitory effect (FIG. 3D), confirming the specificity of the response.

The costimulatory activity of the hB7-H1-specific mAb was very similar to that of the autoantibodies isolated from RA patients, which induced both phenotypic T cell changes and distinct patterns of cytokine secretion described below. Specifically, hB7-H1-specific mAb induced high-levels of CD25 expression on CD4+ T cells, an effect similar to that obtained using a combination of anti-CD3 and anti-CD28 mAbs (FIG. 3E). Additionally, costimulation with anti-CD3 and anti-hB7-H1 mAbs led to increased secretion of IL-10 (FIG. 3F). A small increase in interferon-γ (IFN-γ) secretion was also observed in culture supernatant, while IL-2 and IL-4 were not detected (data not shown). Taken together, these results suggest a reverse signaling function of B7-H1 on CD4+ T cells.

Example 5

Enhancement of Apoptosis of Activated CD4+ T Cells by B7-H1-specific mAb

One activity of B7-H1-specific mAb is to enhance proliferation of CD4+ T cells in response to TCR ligation. This suggests that the hB7-H1-specific autoantibodies in RA patients may contribute to the persistent activation of newly recruited T cells when they encounter self-antigens. In RA patients, however, many CD4+ T cells are already activated. The effect of B7-H1 triggering by antibodies on activated T cells may be different from those observed on primary T cells. To examine the effect of hB7-H1 mAb on activated CD4+ T cells, a culture system in which optimal doses of anti-CD3 mAb can drive T cell proliferation without additional costimulation was employed. In this setting, hB7-H1-specific mAb significantly increased apoptosis of CD4+ T cells as determined by staining the cells with propidium iodide (PI) and Annexin V (FIG. 4A). The cell death induced by the hB7-H1-specific mAb was completely abrogated by pre-incubation of the mAb with B7-H1Ig, but not by pre-incubation with control Ig (FIG. 4B). Immobilized PD-1Ig also increased apoptosis of activated T cells (FIG. 4A). Neither soluble nor immobilized B7-H1-specific mAb or PD-1Ig alone had this effect (data not shown).

To define the mechanism of the apoptotic effect, DNA arrays were used to analyze the expression of apoptosis-related genes stimulated by hB7-H1-specific mAb. Up to seventy-two hours following ligation with immobilized anti-CD3 and anti-hB7-H1 mAbs, mRNA from CD4+ T cells was extracted and $^{32}$P-labeled cDNA made from it was hybridized to a DNA superarray membrane. In three separate experiments, transcription of caspase-10 and caspase-3 genes was reproducibly increased by the anti-CD3/anti-hB7-H1 treatment (FIG. 4C). The expression of tumor necrosis factor-related apoptosis-inducing ligand (TRAIL) was similarly upregulated (FIG. 4C).

Enhanced gene expression was also confirmed by protein analysis. Specifically, using FFC analysis, elevated levels of TRAIL were observed on anti-CD3/anti-hB7-H1 mAb stimulated CD4+ T cells by staining with anti-TRAIL antibody (FIG. 4D). Significant increases of active caspase-3 were similarly detected after 48 and 72 hrs of stimulation (FIG. 4E). Neither B7-H1 mAb nor anti-CD3 (at a suboptimal dose) alone stimulated these changes. Anti-CD3 mAb at a high dose (1 µg/ml), however, did induce the activation of caspase 3 but not the expression of TRAIL in activated CD4+ T cells (data not shown). These observations emphasize dependence on a TCR signal of the effect of B7-H1 mAb. The above data show that hB7-H1-specific mAb upregulates caspases and TRAIL on CD4+ T cells. These proteins likely facilitate activation-induced apoptosis of the CD4+ T cells.

The same apoptotic effects, but to a lesser degree, were seen with human CD8+ T cells.

IL-10 is a potent immunosuppressive cytokine that stimulates Th2 CD4+ T cell responses and enhances the apoptosis of activated T cells [Goergescu et al. (1997) J. Clin. Invest. 100:2622-2633; Saito et al. (1999) J. Immunol. 162:2488-2492; Mignon-Godefroy et al. (1995) J. Immunol. 154: 6634-6643; Clerici et al. (1994) Proc. Natl. Acad. Sci. USA 91:11811-11815]. hB7-H1-specific mAb stimulated secretion of IL-10 from activated CD4+ T cells (FIG. 3F), providing evidence that IL-10 might play a role in the increased apoptosis induced by B7-H1 mAb. In order to test this idea directly, whether neutralization of IL-10 in anti-CD3/anti-hB7-H1 mAb-stimulated CD4+ T cell cultures inhibited apoptosis was examined. As shown in FIG. 4F, inclusion of anti-IL-10 mAb significantly reduced the amount of apoptosis induced by combined anti-CD3 and anti-hB7-H1 mAb treatment at 72 hours. In contrast, neutralizing antibodies against Fas ligand and IL-2 had no effect. These findings indicate that IL-10 facilitates, at least in part, the induction of apoptosis by B7-H1 mAb ligation.

A number of embodiments of the invention have been described. Nevertheless, it will be understood that various modifications may be made without departing from the spirit and scope of the invention. Accordingly, other embodiments are within the scope of the following claims.

What is claimed is:

1. A method of diagnosis, comprising:
   (a) identifying a subject that is suspected of having an autoimmune disease;
   (b) obtaining a sample of body fluid from the subject; and
   (c) testing for the presence in the sample of one or more antibodies that bind to human wild-type B7-H1,
   wherein an elevated level in the sample of one or more antibodies that bind to human wild-type B7-H1 is an indication that the subject has an autoimmune disease.

2. The method of claim 1, wherein the autoimmune disease is rheumatoid arthritis.

3. The method of claim 1, wherein the autoimmune disease is systemic lupus erythematosus.

4. The method of claim 1, wherein the autoimmune disease is autoimmune hearing loss.

5. The method of claim 1, wherein the body fluid is blood.

6. A method of monitoring the progress of a disease, comprising:
   (a) identifying a subject that is suspected of having an autoimmune disease;
   (b) obtaining a sample of body fluid from the subject; and
   (c) testing for the presence in the sample of one or more antibodies that bind to human wild-type B7-H1,
   wherein an elevated level in the sample of one or more antibodies that bind to human wild-type B7-H1 is an indication that the subject has an autoimmune disease and directly correlates with the existence of the active stage of the autoimmune disease.

7. The method of claim 6, further comprising repeating steps (b) and (c) one or more times.

8. The method of claim 6, wherein the autoimmune disease is rheumatoid arthritis.

9. The method of claim 6, wherein the autoimmune disease is systemic lupus erythematosus.

10. The method of claim 6, wherein the autoimmune disease is autoimmune hearing loss.

11. The method of claim 6, wherein the body fluid is blood.

* * * * *